United States Patent
Zhang et al.

(10) Patent No.: US 10,774,135 B2
(45) Date of Patent: Sep. 15, 2020

(54) VARIANT ANTIBODIES THAT BIND AIP2

(71) Applicant: Sorrento Therapeutics, Inc., San Diego, CA (US)

(72) Inventors: Yanliang Zhang, San Diego, CA (US); Gunnar F. Kaufmann, San Diego, CA (US)

(73) Assignee: Sorrento Therapeutics, Inc., San Diego, CA (US)

( * ) Notice: Subject to any disclaimer, the term of this patent is extended or adjusted under 35 U.S.C. 154(b) by 0 days.

(21) Appl. No.: 16/228,570

(22) Filed: Dec. 20, 2018

(65) Prior Publication Data

US 2019/0194300 A1 Jun. 27, 2019

Related U.S. Application Data

(60) Provisional application No. 62/609,760, filed on Dec. 22, 2017.

(51) Int. Cl.
  *C07K 16/12* (2006.01)
  *A61K 39/00* (2006.01)

(52) U.S. Cl.
  CPC .... *C07K 16/1271* (2013.01); *A61K 2039/505* (2013.01); *C07K 2317/21* (2013.01); *C07K 2317/33* (2013.01); *C07K 2317/55* (2013.01); *C07K 2317/567* (2013.01); *C07K 2317/622* (2013.01); *C07K 2317/92* (2013.01); *C07K 2317/94* (2013.01)

(58) Field of Classification Search
  None
  See application file for complete search history.

(56) References Cited

U.S. PATENT DOCUMENTS

| | | | | |
|---|---|---|---|---|
| 8,859,740 | B2 * | 10/2014 | Kaufmann | C07K 16/1271 530/387.3 |
| 9,631,009 | B2 | 4/2017 | Kaufmann et al. | |
| 10,472,413 | B2 | 11/2019 | Kaufmann et al. | |
| 2010/0291093 | A1 | 11/2010 | Janda et al. | |
| 2012/0107327 | A1 | 5/2012 | Anderson et al. | |

FOREIGN PATENT DOCUMENTS

| WO | WO 2011/127032 A1 | 10/2011 |
|---|---|---|
| WO | WO 2014/066677 A1 | 5/2014 |

OTHER PUBLICATIONS

Park, et al., "Infection Control by Antibody Disruption of Bacterial Quorum Sensing Signaling," 2007, Chemical Biology 14(10):1119-1127.
Kirchdoerfer, et al., "Structural Basis for Ligand Recognition and Discrimination of a Quorum-Quenching Antibody," 2011 The Journal of Biological Chemistry 286(19):17351-17358.
Bendig M. M., "Humanization of Rodent Monoclonal Antibodies by CDR Grafting," Methods: A Companion to Methods in Enzymology, 8:83-93, 1995.
Casset et al., "A peptide mimetic of an anti-CD4 monoclonal antibody by rational design," Biochemical and Biophysical Research Communications, 307:198-205, 2003.
Chien et al., "Significant structural and functional change of an antigen-binding site by a distant amino acid substitution: Proposal of a structural mechanism," Proc. Natl. Acad. Sci., 86(14):5532-5536, 1989.
Colman P. M., "Effects of amino acid sequence changes on antibody-antigen interactions," Research in Immunology, 145:33-36, 1994.
Kaufmann et al., "Generation of Quorum Quenching Antibodies" Chap 22 Quorum Sensing: Methods and Protocols, Methods in Molecular Biology, vol. 692, DOI 10.1007/978-1-60761-971-0_22, © Springer Science+Business Media, LLC, 2011.
Kobrin et al., "A V Region Mutation in a Phosphocholine-Binding Monoclonal Antibody Results in Loss of Antigen Binding," Journal of Immunology, 146(6):2017-2020, 1991.
Lederman et al., "A Single Amino Acid Substitution in a Common African Allele of the CD4 Molecule Ablates Binding of the Monoclonal Antibody, PKT4," Molecular Immunology, 28:1171-1181, 1991.
Li et al., "b-Endorphin omission analogs: Dissociation of immunoreactivity from other biological activities," Proc. Natl. Acad. Sci. USA, 77:3211-3214, 1980.
Lyon et al., "Rational design of a global inhibitor of the virulence response in Staphylococcus aureus, based in part on localization of the site of inhibition to the receptor-histidine kinase, AgrC," PNAS, 97:13330-13335, 2000.
Lyon et al., "Peptide signaling in Staphylococcus aureus and other Gram-positive bacteria," Peptides, 25 (9):1389-1403, 2004.
MacCallum et al., "Antibody-antigen Interactions: Contact Analysis and Binding Site Topography," J. Mol. Biol., 262,732-745, 1996.
Panka et al., "Defining the Structural Correlates Responsible for Loss of Arsenate Affinity in an IdCR Antibody Isolated From an Autoimmune Mouse," Molecular Immunology, 30(11):1013-1020, 1993.
Paul, Fundamental Immunology, 3rd edition, 1993, pp. 292-295.
Rudikoff et al., "Single amino acid substitution altering antigen-binding specificity," Proc. Natl. Acad. Sci. USA, 79 (6):1979-1983, 1982.
Winkler et al., "Changing the Antigen Binding Specificity by Single Point Mutations of an Anti-p24 (HIV-1) Antibody1," Journal of Immunology, 165(8):4505-4514, 2000.
International Search Report and Written Opinion for PCT/US2013/066675 dated Feb. 7, 2014.

* cited by examiner

*Primary Examiner* — Brian Gangle
(74) *Attorney, Agent, or Firm* — McNeill Baur PLLC

(57) ABSTRACT

The present disclosure provides fully human variant anti-AIP2 variant antibodies, and antigen binding proteins thereof, having improved characteristics compared to the wild type anti-AIP2 antibody E7 from which the variant clones are derived. The variant anti-AIP2 antibodies exhibit improved binding to AIP1 and AIP4 as determined in an in vitro quorum sensing reporter assay, have improved thermal stability, provided complete protection against infection with two different strains of Staphylococcus aureus MRSA in pre-treated mice, and can be manufactured at higher yields.

13 Claims, 5 Drawing Sheets

Specification includes a Sequence Listing.

Fig. 2

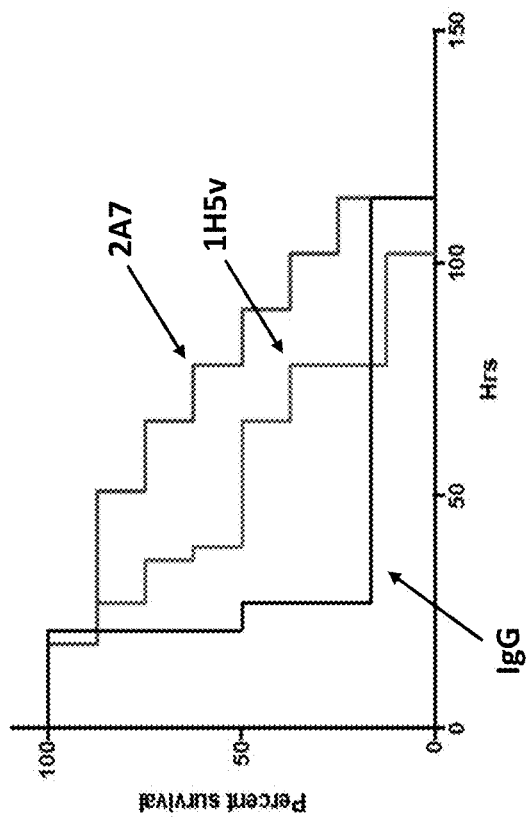

VARIANT ANTIBODIES THAT BIND AIP2

This application claims the benefit of priority under 35 U.S.C. § 0119 to U.S. provisional application No. 62/609,760, filed Dec. 22, 2017, and entitled "Improved Variant Antibodies that Bind AIP2", the contents of which is incorporated by reference herein in its entirety.

This invention was made with the support of grant 5 R42 AI098182-04 from the National Institutes of Health. The federal government may have certain rights to this invention.

Throughout this application various publications, patents, and/or patent applications are referenced. The disclosures of the publications, patents and/or patent applications are hereby incorporated by reference in their entireties into this application in order to more fully describe the state of the art to which this disclosure pertains.

SEQUENCE LISTING

The instant application contains a Sequence Listing which has been filed electronically in ASCII format and is hereby incorporated by reference in its entirety. Said ASCII copy, created on Dec. 18, 2018, is named S103014_2070US_1_(910_1)_SL.txt and is 13,858 bytes in size.

TECHNICAL FIELD

The present disclosure provides variant anti-AIP2 IgG class antibodies that differ in their amino acid sequence compared to a wild type anti-AIP2 antibody. The variant antibodies bind AIP2 and exhibit improved characteristics compared to the wild type antibody, including improved binding to AIP1 and AIP4, improved thermal stability, provide protection against infection with two different strains of *Staphylococcus aureus* MRSA in pre-treated mice, and can be manufactured at higher yields. More specifically, the present disclosure provides human antibodies that bind AIP2, AIP2-binding fragments and derivatives of such antibodies, and AIP2-binding polypeptides comprising such fragments. The disclosed variant antibodies are particularly useful to treat bacterial infections, such as those infections caused by *Staphylococcus aureus* and a MRSA strain.

BACKGROUND

Ever since it was first discovered by Sir Alexander Ogston in 1880, *Staphylococcus aureus* has been regarded as a serious threat to human health, capable of causing a multitude of infections. The rise of antibiotic-resistant strains in the 1960s and 1970s, particularly methicillin-resistant *S. aureus* (MRSA), has created additional therapeutic challenges. Currently, MRSA strains account for >50% of all *S. aureus* isolates causing clinical disease in the US. This is a much higher percentage compared to other countries, such as France at 14.5% and the Netherlands at 3.1%. In a review of 31 observational studies from Western Europe, the authors found that the percentage of MRSA among *S. aureus* clinical isolates ranged between 5% and 54%, but was limited by the different methodologies used in the studies.

Methicillin-resistant *Staphylococcus aureus* (MRSA) is a bacterium responsible for several difficult-to-treat infections in humans. It is also called multidrug-resistant *Staphylococcus aureus* and oxacillin-resistant *Staphylococcus aureus* (ORSA). MRSA is any strain of *Staphylococcus aureus* that has developed resistance to beta-lactam antibiotics, which include the penicillins (such as methicillin, dicloxam, naf- cillin and oxacillin) and the cephalosporins. Strains unable to resist these antibiotics are classified as methicillin-sensitive *Staphylococcus aureus* (MSSA). The development of such resistance does not cause the organism to be more intrinsically virulent than strains of *Staphylococcus aureus* that have no antibiotic resistance, but resistance does make MRSA infection more difficult to treat with standard types of antibiotics and thus more dangerous.

MRSA is especially troublesome in hospitals, prisons, schools, and nursing homes, where patients with open wounds, invasive devices, and weakened immune systems are at greater risk of infection than the general public.

MRSA strains are prevalent bacterial pathogens that cause both health care- and community-associated infections. Increasing resistance to commonly prescribed antibiotics has made MRSA a serious threat to public health throughout the world. The USA300 strain of MRSA has been responsible for an epidemic of community-associated infections in the US, mostly involving skin and soft tissue but also more serious invasive syndromes such as pneumonia, severe sepsis and endocarditis. MRSA strains are particularly serious and potentially lethal pathogens that possess virulence mechanisms including toxins, adhesins, enzymes and immunomodulators. One of these is Panton-Valentine leukocidin (PVL), a toxin associated with abscess formation and severe necrotizing pneumonia.

Initially, MRSA strains afflicted hospitalized patients and those with chronic illnesses. The 1990s saw the emergence of community-associated MRSA (CA-MRSA) strains that primarily caused skin and soft tissue infections (SSTIs) in otherwise healthy individuals, often children. These strains quickly led to an epidemic of CA-MRSA infections including some with severe consequences, for example, community-acquired pneumonia with high mortality rates. The high prevalence of CA-MRSA among infecting MRSA strains in the US is mostly due to the Panton-Valentine leukocidin (PVL)-positive USA300 clone, while in Europe the predominant strain of CA-MRSA is a PVL-positive ST80 clone. A mathematical model predicted that CA-MRSA will become the dominant MRSA strain in hospitals because of the expanding community reservoir, CA-MRSA strains are more fit (higher replicative capacity) than hospital-associated types and that CA-MRSA infections will become increasingly severe (D'Agata et al., Clin. Infect. Dis. 48, 274-284, 2009).

Agents directed against the virulence mechanisms of MRSA strains would have several advantages compared to antibiotics. First, there would be no selective pressure exerted on other nonpathogenic, commensal bacteria. Second, the associated toxicities of antibiotics (e.g. allergic reactions, nephrotoxicity and *Clostridium difficile* infection) may be avoided. Third, limiting antibiotics may decrease the development of drug-resistant bacteria. Combining anti-virulence therapies with traditional antibiotics has the potential to change the paradigm of how MRSA infections are managed. Since bacterial survival is not impacted by the function of its virulence mechanisms, it is possible that resistance to anti-virulence therapy would be slow to develop. One potential strategy is to inhibit the accessory gene regulator (agr) operon. In vitro experiments have shown that variants of autoinducing peptide (AIP) inhibit AgrC function. An in vivo study demonstrated that administering AIP-2 concurrently with an agr type 1 strain reduced abscess formation (Wright et al., Proc. Natl. Acad. Sci. USA 102, 1691-1696, 2005). However, agr inhibitors can promote biofilm formation, which could result in chronic *S.* aureus infections (Beenken et al., PLoS ONE 5, e10790, 2010). Hence, further investigation on this approach is needed.

Another strategy for devices is the use of nanomaterials, defined as materials with at least one dimension less than 100 nm, to prevent the formation of biofilms (Taylor & Webster, Int. J. Nanomedicine 6, 1463-1473, 2011). Silver-Page lined urinary catheters and central venous catheters are used in clinical practice to lower the risk of health care-associated infections (Raad et al., Antimicrob. Agents Chemother. 56, 935-941, 2012). Decreasing the particle size of silver down to the nanometre range increases the surface area, which improves the antibacterial activity of the material (Taylor & Webster, Int. J. Nanomedicine 6, 1463-1473, 2011). Staphyloxanthin is a pigment of S. aureus that helps it resist reactive oxygen species such as those released by neutrophils. Early steps in staphyloxanthin production are similar to those in cholesterol production. A human squalene synthase inhibitor blocked staphyloxanthin biosynthesis in vitro, resulting in nonpigmented bacteria that were more susceptible to killing by human blood and clearance by the innate immune system in a mouse model (Liu et al., Science 319, 1391-1394, 2008). Statins were shown to enhance S. aureus clearance by phagocytes through production of antibacterial DNA-based extracellular traps by human and murine neutrophils, macrophages and monocytes (Chow et al., Cell Host Microbe 8, 445-454, 2010).

For CA-MRSA infections, one specific target is PVL toxin, and antibody against it is under investigation as a potential vaccine. However, in a study on antibody levels against PVL in children with PVL-positive MRSA infections, neutralizing antibody against PVL was not protective against primary or recurrent CA-MRSA skin infections (Hermos et al., Clin. Infect. Dis. 51, 1138-1146, 2010). Other investigators, using a murine model of dermonecrosis, evaluated an agonist of human C5a called EP67 for its ability to induce host immunity against CA-MRSA (Sheen et al., Vaccine 30, 9-13, 2011). EP67 was effective in limiting the infection through the promotion of cytokine synthesis and neutrophil influx. This promising finding may warrant further investigation in humans.

Peptidoglycan (PG) comprises approximately 50% of the cell wall of S. aureus. A PG-based vaccine against S. aureus, A170PG, was shown to be protective in a mouse model against several strains of MRSA including A174, A175, A176 and RIMD31092 (Capparelli et al., PLoS ONE 6, e28377, 2011). The protection correlated with increased survival and reduced colonization and lasted at least 40 weeks. One caveat with this study is that the mouse strain used does not closely mimic human infection because mice do not have pre-existing antibodies to S. aureus. In June 2011, Merck and Intercell announced the termination of phase II/III development of V170, a subunit vaccine containing the S. aureus antigen IsdB, which is a cell surface localized iron-regulated protein (Etz et al., Proc. Natl. Acad. Sci. USA 99, 6573-6578, 2002). Safety concerns were cited due to an increase in overall mortality and multi-organ dysfunction in the vaccine recipients compared to those who received placebo.

Thus, there remains a need in the art for effective treatments based on AIP2, particularly anti-AIP2 antibodies. The present disclosure provides improved variant antibody sequences compared to its parent fully human wild type sequence.

SUMMARY

The present disclosure provides anti-AIP2 variant clone antibodies, and antigen binding proteins thereof, having improved capabilities for inhibiting pathogenic bacterial quorum sensing (QS) compared to the wild type anti-AIP2 antibody E7 from which the variant clones are derived. In one embodiment, the anti-AIP2 antibodies comprise fully human antibodies. Fab fully human antibody fragments, and single chain human antibodies.

The present disclosure provides a fully human antibody of an IgG class that binds to Staphylococcus aureus autoinducing peptide-2 (AIP2), wherein the antibody comprises heavy chain/light chain variable domain amino acid sequences that are at least 95% identical to the heavy/light chain variable domain amino acid sequences selected from the group consisting of SEQ ID NO: 3 for heavy chain/SEQ ID NO: 2 for the light chain for 1G3; SEQ ID NO:4 for heavy chain/SEQ ID NO:2 for the light chain for 2A7; SEQ ID NO:5 for heavy chain/SEQ ID NO:2 for the light chain for 2B12; SEQ ID NO:6 for heavy chain/SEQ ID NO:2 for the light chain for 2(E)6; SEQ ID NO:7 for heavy chain/SEQ ID NO:2 for the light chain for 2H5; SEQ ID NO:8 for heavy chain/SEQ ID NO:9 for the light chain for X18; SEQ ID NO:10 for heavy chain/SEQ ID NO:11 for the light chain for X12; and SEQ ID NO: 12 for heavy chain/SEQ ID NO:9 for the light chain for 2H5V.

The present disclosure provides a fully human antibody of an IgG class that binds to Staphylococcus aureus autoinducing peptide-2 (AIP2) epitope, comprising an antibody selected from the group consisting of 1G3, 2A7, 2B12, 2(E)6, 2H5, X18, X12 and 2H5 variant. In one embodiment, the heavy chain/light chain sequence sets include: SEQ ID NO: 3 for heavy chain/SEQ ID NO: 2 for the light chain for 1G3; SEQ ID NO:4 for heavy chain/SEQ ID NO:2 for the light chain for 2A7; SEQ ID NO:5 for heavy chain/SEQ ID NO:2 for the light chain for 2B12; SEQ ID NO:6 for heavy chain/SEQ ID NO:2 for the light chain for 2(E)6; SEQ ID NO:7 for heavy chain/SEQ ID NO:2 for the light chain for 2H5; SEQ ID NO:8 for heavy chain/SEQ ID NO:9 for the light chain for X18; SEQ ID NO:10 for heavy chain/SEQ ID NO:11 for the light chain for X12; and SEQ ID NO: 12 for heavy chain/SEQ ID NO:9 for the light chain for 2H5V.

In one embodiment, the fully human antibody of an IgG class that binds to Staphylococcus aureus autoinducing peptide-2 (AIP2) exhibits a $K_d$ of less than 100 nM, or less than 50 nM, or less than 10 nM, or less than 1 nM, or less than 0.1 nM, or less than 0.01 nM. In one embodiment, the fully human anti-AIP2 antibody X12 has a $K_d$ of $6.49 \times 10^{-8}$ as measured by surface plasmon resonance. In one embodiment, the fully human anti-AIP2 antibody X18 has a $K_d$ of $3.5 \times 10^{-8}$ as measured by surface plasmon resonance.

In one embodiment, the fully human anti-AIP2 antibody binds a quorum sensing molecule autoinducing peptide-2 (AIP2) produced by Staphylococcus aureus and suppresses AIP2 signaling in Staphylococcus aureus.

In one embodiment, the fully human anti-AIP2 antibodies 2A7, 2H5v and X18 bind to autoinducing peptide-2 (AIP2) from a strain group I of Staphylococcus aureus. In one embodiment, the fully human anti-AIP2 antibodies X12 and X18 bind to autoinducing peptide-2 (AIP2) from a strain group II of Staphylococcus aureus. In one embodiment, the fully human anti-AIP2 antibodies 2H5, 1g3 and X18 bind to autoinducing peptide-2 (AIP2) from a strain group IV of Staphylococcus aureus.

In one embodiment, the fully human antibody of an IgG class that binds to Staphylococcus aureus autoinducing peptide-2 (AIP2) is a labeled antibody that comprises a detectable label or detectable moiety.

The present disclosure provides a nucleic acid encoding the fully human antibody of an IgG class that binds to

*Staphylococcus aureus* autoinducing peptide-2 (AIP2), wherein the antibody comprises heavy chain/light chain variable domain amino acid sequences that are at least 95% identical to the heavy/light chain variable domain amino acid sequences selected from the group consisting of SEQ ID NO: 3 for heavy chain/SEQ ID NO: 2 for the light chain for 1G3; SEQ ID NO:4 for heavy chain/SEQ ID NO:2 for the light chain for 2A7; SEQ ID NO:5 for heavy chain/SEQ ID NO:2 for the light chain for 2B12; SEQ ID NO:6 for heavy chain/SEQ ID NO:2 for the light chain for 2(E)6; SEQ ID NO:7 for heavy chain/SEQ ID NO:2 for the light chain for 2H5; SEQ ID NO:8 for heavy chain/SEQ ID NO:9 for the light chain for X18; SEQ ID NO:10 for heavy chain/SEQ ID NO:11 for the light chain for X12; and SEQ ID NO: 12 for heavy chain/SEQ ID NO:9 for the light chain for 2H5V.

The present disclosure provides a nucleic acid encoding the fully human antibody of an IgG class that binds to *Staphylococcus aureus* autoinducing peptide-2 (AIP2), wherein the antibody comprises heavy chain/light chain variable domain amino acid sequences selected from the group consisting of SEQ ID NO: 3 for heavy chain/SEQ ID NO: 2 for the light chain for 1G3; SEQ ID NO:4 for heavy chain/SEQ ID NO:2 for the light chain for 2A7; SEQ ID NO:5 for heavy chain/SEQ ID NO:2 for the light chain for 2B12; SEQ ID NO:6 for heavy chain/SEQ ID NO:2 for the light chain for 2(E)6; SEQ ID NO:7 for heavy chain/SEQ ID NO:2 for the light chain for 2H5; SEQ ID NO:8 for heavy chain/SEQ ID NO:9 for the light chain for X18; SEQ ID NO:10 for heavy chain/SEQ ID NO:11 for the light chain for X12; and SEQ ID NO: 12 for heavy chain/SEQ ID NO:9 for the light chain for 2H5V.

The present disclosure provides a vector comprising the nucleic acid encoding any of the fully human antibody an IgG class that binds to *Staphylococcus aureus* autoinducing peptide-2 (AIP2), or antigen binding proteins thereof.

The present disclosure provides a host cell harboring the vector which comprises a nucleic acid encoding any of the fully human antibody an IgG class that binds to *Staphylococcus aureus* autoinducing peptide-2 (AIP2), or antigen binding proteins thereof. In one embodiment, the host cell is transfected or transformed with the vector comprising the nucleic acid.

The present disclosure provides a pharmaceutical composition comprising the fully human antibody an IgG class that binds to *Staphylococcus aureus* autoinducing peptide-2 (AIP2), or antigen binding proteins thereof. In one embodiment, the pharmaceutical composition comprises a pharmaceutically acceptable carrier.

The present disclosure provides a Fab fully human antibody that binds to *Staphylococcus aureus* autoinducing peptide-2 (AIP2), wherein the antibody comprises heavy chain/light chain variable domain amino acid sequences that are at least 95% identical to the heavy/light chain variable domain amino acid sequences selected from the group consisting of SEQ ID NO: 3 for heavy chain/SEQ ID NO: 2 for the light chain for 1G3; SEQ ID NO:4 for heavy chain/SEQ ID NO:2 for the light chain for 2A7; SEQ ID NO:5 for heavy chain/SEQ ID NO:2 for the light chain for 2B12; SEQ ID NO:6 for heavy chain/SEQ ID NO:2 for the light chain for 2(E)6; SEQ ID NO:7 for heavy chain/SEQ ID NO:2 for the light chain for 2H5; SEQ ID NO:8 for heavy chain/SEQ ID NO:9 for the light chain for X18; SEQ ID NO:10 for heavy chain/SEQ ID NO:11 for the light chain for X12; and SEQ ID NO: 12 for heavy chain/SEQ ID NO:9 for the light chain for 2H5V.

The present disclosure provides a Fab fully human antibody that binds to an AIP2 epitope, comprising an antibody selected from the group consisting of 1G3, 2A7, 2B12, 2(E)6, 2H5, X18, X12 and 2H5 variant. In one embodiment, the heavy chain/light chain sequence sets include: SEQ ID NO: 3 for heavy chain/SEQ ID NO: 2 for the light chain for 1G3; SEQ ID NO:4 for heavy chain/SEQ ID NO:2 for the light chain for 2A7; SEQ ID NO:5 for heavy chain/SEQ ID NO:2 for the light chain for 2B12; SEQ ID NO:6 for heavy chain/SEQ ID NO:2 for the light chain for 2(E)6; SEQ ID NO:7 for heavy chain/SEQ ID NO:2 for the light chain for 2H5; SEQ ID NO:8 for heavy chain/SEQ ID NO:9 for the light chain for X18; SEQ ID NO:10 for heavy chain/SEQ ID NO:11 for the light chain for X12; and SEQ ID NO: 12 for heavy chain/SEQ ID NO:9 for the light chain for 2H5V.

In one embodiment, the Fab fully human antibody that binds to *Staphylococcus aureus* autoinducing peptide-2 (AIP2) exhibits a $K_d$ of less than 100 nM, or less than 50 nM, or less than 10 nM, or less than 1 nM, or less than 0.1 nM, or less than 0.01 nM.

In one embodiment, the fully human anti-AIP2 antibody binds a quorum sensing molecule autoinducing peptide-2 (AIP2) produced by *Staphylococcus aureus* and suppresses AIP2 signaling in *Staphylococcus aureus*.

In one embodiment, the Fab fully human anti-AIP2 antibodies 2A7, 2H5v and X18 bind to autoinducing peptide-2 (AIP2) from a strain group I of *Staphylococcus aureus*. In one embodiment, the Fab fully human anti-AIP2 antibodies X12 and X18 bind to autoinducing peptide-2 (AIP2) from a strain group II of *Staphylococcus aureus*. In one embodiment, the Fab fully human anti-AIP2 antibodies 2H5, 1g3 and X18 bind to autoinducing peptide-2 (AIP2) from a strain group IV of *Staphylococcus aureus*.

In one embodiment, the Fab fully human antibody that binds to *Staphylococcus aureus* autoinducing peptide-2 (AIP2) is a labeled antibody that comprises a detectable label or detectable moiety.

The present disclosure provides a nucleic acid encoding the Fab fully human antibody that binds to *Staphylococcus aureus* autoinducing peptide-2 (AIP2), wherein the antibody comprises heavy chain/light chain variable domain amino acid sequences that are at least 95% identical to the heavy/light chain variable domain amino acid sequences selected from the group consisting of SEQ ID NO: 3 for heavy chain/SEQ ID NO: 2 for the light chain for 1G3; SEQ ID NO:4 for heavy chain/SEQ ID NO:2 for the light chain for 2A7; SEQ ID NO:5 for heavy chain/SEQ ID NO:2 for the light chain for 2B12; SEQ ID NO:6 for heavy chain/SEQ ID NO:2 for the light chain for 2(E)6; SEQ ID NO:7 for heavy chain/SEQ ID NO:2 for the light chain for 2H5; SEQ ID NO:8 for heavy chain/SEQ ID NO:9 for the light chain for X18; SEQ ID NO:10 for heavy chain/SEQ ID NO:11 for the light chain for X12; and SEQ ID NO: 12 for heavy chain/SEQ ID NO:9 for the light chain for 2H5V.

The present disclosure provides a nucleic acid encoding the Fab fully human antibody that binds to *Staphylococcus aureus* autoinducing peptide-2 (AIP2), wherein the antibody comprises heavy chain/light chain variable domain amino acid sequences selected from the group consisting of SEQ ID NO: 3 for heavy chain/SEQ ID NO: 2 for the light chain for 1G3; SEQ ID NO:4 for heavy chain/SEQ ID NO:2 for the light chain for 2A7; SEQ ID NO:5 for heavy chain/SEQ ID NO:2 for the light chain for 2B12; SEQ ID NO:6 for heavy chain/SEQ ID NO:2 for the light chain for 2(E)6; SEQ ID NO:7 for heavy chain/SEQ ID NO:2 for the light chain for 2H5; SEQ ID NO:8 for heavy chain/SEQ ID NO:9 for the light chain for X18; SEQ ID NO:10 for heavy chain/SEQ ID NO:11 for the light chain for X12; and SEQ ID NO: 12 for heavy chain/SEQ ID NO:9 for the light chain for 2H5V.

The present disclosure provides a vector comprising the nucleic acid encoding any of the Fab fully human antibody that binds to *Staphylococcus aureus* autoinducing peptide-2 (AIP2), or antigen binding proteins thereof.

The present disclosure provides a host cell harboring the vector which comprises a nucleic acid encoding any of the Fab fully human antibody that binds to *Staphylococcus aureus* autoinducing peptide-2 (AIP2), or antigen binding proteins thereof. In one embodiment, the host cell is transfected or transformed with the vector comprising the nucleic acid.

The present disclosure provides a pharmaceutical composition comprising the Fab fully human antibody that binds to *Staphylococcus aureus* autoinducing peptide-2 (AIP2), or antigen binding proteins thereof. In one embodiment, the pharmaceutical composition comprises a pharmaceutically acceptable carrier.

The present disclosure provides a single chain fully human antibody that binds to *Staphylococcus aureus* autoinducing peptide-2 (AIP2), wherein the antibody comprises heavy chain/light chain variable domain amino acid sequences that are at least 95% identical to the heavy/light chain variable domain amino acid sequences selected from the group consisting of SEQ ID NO: 3 for heavy chain/SEQ ID NO: 2 for the light chain for 1G3; SEQ ID NO:4 for heavy chain/SEQ ID NO:2 for the light chain for 2A7; SEQ ID NO:5 for heavy chain/SEQ ID NO:2 for the light chain for 2B12; SEQ ID NO:6 for heavy chain/SEQ ID NO:2 for the light chain for 2(E)6; SEQ ID NO:7 for heavy chain/SEQ ID NO:2 for the light chain for 2H5; SEQ ID NO:8 for heavy chain/SEQ ID NO:9 for the light chain for X18; SEQ ID NO:10 for heavy chain/SEQ ID NO:11 for the light chain for X12; and SEQ ID NO: 12 for heavy chain/SEQ ID NO:9 for the light chain for 2H5V.

The present disclosure provides a single chain fully human antibody that binds to an AIP2 epitope, comprising an antibody selected from the group consisting of 1G3, 2A7, 2B12, 2(E)6, 2H5, X18, X12 and 2H5 variant. In one embodiment, the heavy chain/light chain sequence sets include: SEQ ID NO: 3 for heavy chain/SEQ ID NO: 2 for the light chain for 1G3; SEQ ID NO:4 for heavy chain/SEQ ID NO:2 for the light chain for 2A7; SEQ ID NO:5 for heavy chain/SEQ ID NO:2 for the light chain for 2B12; SEQ ID NO:6 for heavy chain/SEQ ID NO:2 for the light chain for 2(E)6; SEQ ID NO:7 for heavy chain/SEQ ID NO:2 for the light chain for 2H5; SEQ ID NO:8 for heavy chain/SEQ ID NO:9 for the light chain for X18; SEQ ID NO:10 for heavy chain/SEQ ID NO:11 for the light chain for X12; and SEQ ID NO: 12 for heavy chain/SEQ ID NO:9 for the light chain for 2H5V.

In one embodiment, the single chain fully human antibody that binds to *Staphylococcus aureus* autoinducing peptide-2 (AIP2) exhibits a $K_d$ of less than 100 nM, or less than 50 nM, or less than 10 nM, or less than 1 nM, or less than 0.1 nM, or less than 0.01 nM.

In one embodiment, the fully human anti-AIP2 antibody binds a quorum sensing molecule autoinducing peptide-2 (AIP2) produced by *Staphylococcus aureus* and suppresses AIP2 signaling in *Staphylococcus aureus*.

In one embodiment, the single chain fully human anti-AIP2 antibodies 2A7, 2H5v and X18 bind to autoinducing peptide-2 (AIP2) from a strain group I of *Staphylococcus aureus*. In one embodiment, the single chain fully human anti-AIP2 antibodies X12 and X18 bind to autoinducing peptide-2 (AIP2) from a strain group II of *Staphylococcus aureus*. In one embodiment, the single chain fully human anti-AIP2 antibodies 2H5, 1g3 and X18 bind to autoinducing peptide-2 (AIP2) from a strain group IV of *Staphylococcus aureus*.

In one embodiment, the single chain fully human antibody that binds to *Staphylococcus aureus* autoinducing peptide-2 (AIP2) is a labeled antibody that comprises a detectable label or detectable moiety.

The present disclosure provides a nucleic acid encoding the single chain fully human antibody that binds to *Staphylococcus aureus* autoinducing peptide-2 (AIP2), wherein the antibody comprises heavy chain/light chain variable domain amino acid sequences that are at least 95% identical to the heavy/light chain variable domain amino acid sequences selected from the group consisting of SEQ ID NO: 3 for heavy chain/SEQ ID NO: 2 for the light chain for 1G3; SEQ ID NO:4 for heavy chain/SEQ ID NO:2 for the light chain for 2A7; SEQ ID NO:5 for heavy chain/SEQ ID NO:2 for the light chain for 2B12; SEQ ID NO:6 for heavy chain/SEQ ID NO:2 for the light chain for 2(E)6; SEQ ID NO:7 for heavy chain/SEQ ID NO:2 for the light chain for 2H5; SEQ ID NO:8 for heavy chain/SEQ ID NO:9 for the light chain for X18; SEQ ID NO:10 for heavy chain/SEQ ID NO:11 for the light chain for X12; and SEQ ID NO: 12 for heavy chain/SEQ ID NO:9 for the light chain for 2H5V.

The present disclosure provides a nucleic acid encoding the single chain fully human antibody that binds to *Staphylococcus aureus* autoinducing peptide-2 (AIP2), wherein the antibody comprises heavy chain/light chain variable domain amino acid sequences selected from the group consisting of SEQ ID NO: 3 for heavy chain/SEQ ID NO: 2 for the light chain for 1G3; SEQ ID NO:4 for heavy chain/SEQ ID NO:2 for the light chain for 2A7; SEQ ID NO:5 for heavy chain/SEQ ID NO:2 for the light chain for 2B12; SEQ ID NO:6 for heavy chain/SEQ ID NO:2 for the light chain for 2(E)6; SEQ ID NO:7 for heavy chain/SEQ ID NO:2 for the light chain for 2H5; SEQ ID NO:8 for heavy chain/SEQ ID NO:9 for the light chain for X18; SEQ ID NO:10 for heavy chain/SEQ ID NO:11 for the light chain for X12; and SEQ ID NO: 12 for heavy chain/SEQ ID NO:9 for the light chain for 2H5V.

The present disclosure provides a vector comprising the nucleic acid encoding any of the single chain fully human antibody that binds to *Staphylococcus aureus* autoinducing peptide-2 (AIP2), or antigen binding proteins thereof.

The present disclosure provides a host cell harboring the vector which comprises a nucleic acid encoding any of the single chain fully human antibody that binds to *Staphylococcus aureus* autoinducing peptide-2 (AIP2), or antigen binding proteins thereof. In one embodiment, the host cell is transfected or transformed with the vector comprising the nucleic acid.

The present disclosure provides a pharmaceutical composition comprising the single chain fully human antibody that binds to *Staphylococcus aureus* autoinducing peptide-2 (AIP2), or antigen binding proteins thereof. In one embodiment, the pharmaceutical composition comprises a pharmaceutically acceptable carrier.

The present disclosure provides a method for binding an anti-AIP2 antibody to an AIP2 antigen, comprising: binding an anti-AIP2 antibody to a *Staphylococcus aureus* autoinducing peptide-2 (AIP2) to form a complex containing the anti-AIP2 antibody bound to the AIP2 antigen, wherein the anti-AIP2 antibody is selected from a group consisting of a fully human antibody of an IgG class, a Fab fully human antibody or a single chain fully human antibody, and wherein the anti-AIP2 antibody comprises a heavy chain/light chain variable domain amino acid sequences which are selected from the group consisting of SEQ ID NO: 3 for heavy chain/SEQ ID NO: 2 for the light chain for 1G3; SEQ ID NO:4 for heavy chain/SEQ ID NO:2 for the light chain for 2A7; SEQ ID NO:5 for heavy chain/SEQ ID NO:2 for the light chain for 2B12; SEQ ID NO:6 for heavy chain/SEQ ID NO:2 for the light chain for 2(E)6; SEQ ID NO:7 for heavy chain/SEQ ID NO:2 for the light chain for 2H5; SEQ ID NO:8 for heavy chain/SEQ ID NO:9 for the light chain for X18; SEQ ID NO:10 for heavy chain/SEQ ID NO:11 for the light chain for X12; and SEQ ID NO: 12 for heavy chain/SEQ ID NO:9 for the light chain for 2H5V. In one embodiment, the anti-AIP2 antibody is a labeled antibody which comprises a detectable label or a detectable moiety. In one embodiment, the method further comprises detecting the complex containing the anti-AIP2 antibody bound to the AIP2 antigen.

The present disclosure provides a method for pre-treating a subject prior to the subject having a *Staphylococcus aureus* infection, the method comprising: administering to the subject an effective amount of an anti-AIP2 antibody, wherein the anti-AIP2 antibody is selected from a group consisting of a fully human antibody of an IgG class, a Fab fully human antibody or a single chain fully human antibody, and wherein the anti-AIP2 antibody comprises a heavy chain/ light chain variable domain amino acid sequences which are selected from the group consisting of SEQ ID NO: 3 for heavy chain/SEQ ID NO: 2 for the light chain for 1G3; SEQ ID NO:4 for heavy chain/SEQ ID NO:2 for the light chain for 2A7; SEQ ID NO:5 for heavy chain/SEQ ID NO:2 for the light chain for 2B12; SEQ ID NO:6 for heavy chain/SEQ ID NO:2 for the light chain for 2(E)6; SEQ ID NO:7 for heavy chain/SEQ ID NO:2 for the light chain for 2H5; SEQ ID NO:8 for heavy chain/SEQ ID NO:9 for the light chain for X18; SEQ ID NO:10 for heavy chain/SEQ ID NO:11 for the light chain for X12; and SEQ ID NO: 12 for heavy chain/SEQ ID NO:9 for the light chain for 2H5V. In one embodiment, the method further comprising: monitoring the subject for any symptoms of infection associated with a *Staphylococcus aureus* autoinducing peptide-2 (AIP2). In one embodiment, the infection associated with a *Staphylococcus aureus* autoinducing peptide-2 (AIP2) comprises Methicillin-resistant *Staphylococcus aureus* (MRSA).

The present disclosure provides a method for treating a subject having a *Staphylococcus aureus* infection, the method comprising: administering to the subject an effective amount of an anti-AIP2 antibody, wherein the anti-AIP2 antibody is selected from a group consisting of a fully human antibody of an IgG class, a Fab fully human antibody or a single chain fully human antibody, and wherein the anti-AIP2 antibody comprises a heavy chain/light chain variable domain amino acid sequences which are selected from the group consisting of SEQ ID NO: 3 for heavy chain/SEQ ID NO: 2 for the light chain for 1G3; SEQ ID NO:4 for heavy chain/SEQ ID NO:2 for the light chain for 2A7; SEQ ID NO:5 for heavy chain/SEQ ID NO:2 for the light chain for 2B12; SEQ ID NO:6 for heavy chain/SEQ ID NO:2 for the light chain for 2(E)6; SEQ ID NO:7 for heavy chain/SEQ ID NO:2 for the light chain for 2H5; SEQ ID NO:8 for heavy chain/SEQ ID NO:9 for the light chain for X18; SEQ ID NO:10 for heavy chain/SEQ ID NO:11 for the light chain for X12; and SEQ ID NO: 12 for heavy chain/SEQ ID NO:9 for the light chain for 2H5V. In one embodiment, the method further comprising: monitoring the subject for any symptoms of infection associated with a *Staphylococcus aureus* autoinducing peptide-2 (AIP2). In one embodiment, the infection associated with a *Staphylococcus aureus* autoinducing peptide-2 (AIP2) comprises Methicillin-resistant *Staphylococcus aureus* (MRSA).

BRIEF DESCRIPTION OF THE FIGURES

Figure 2:
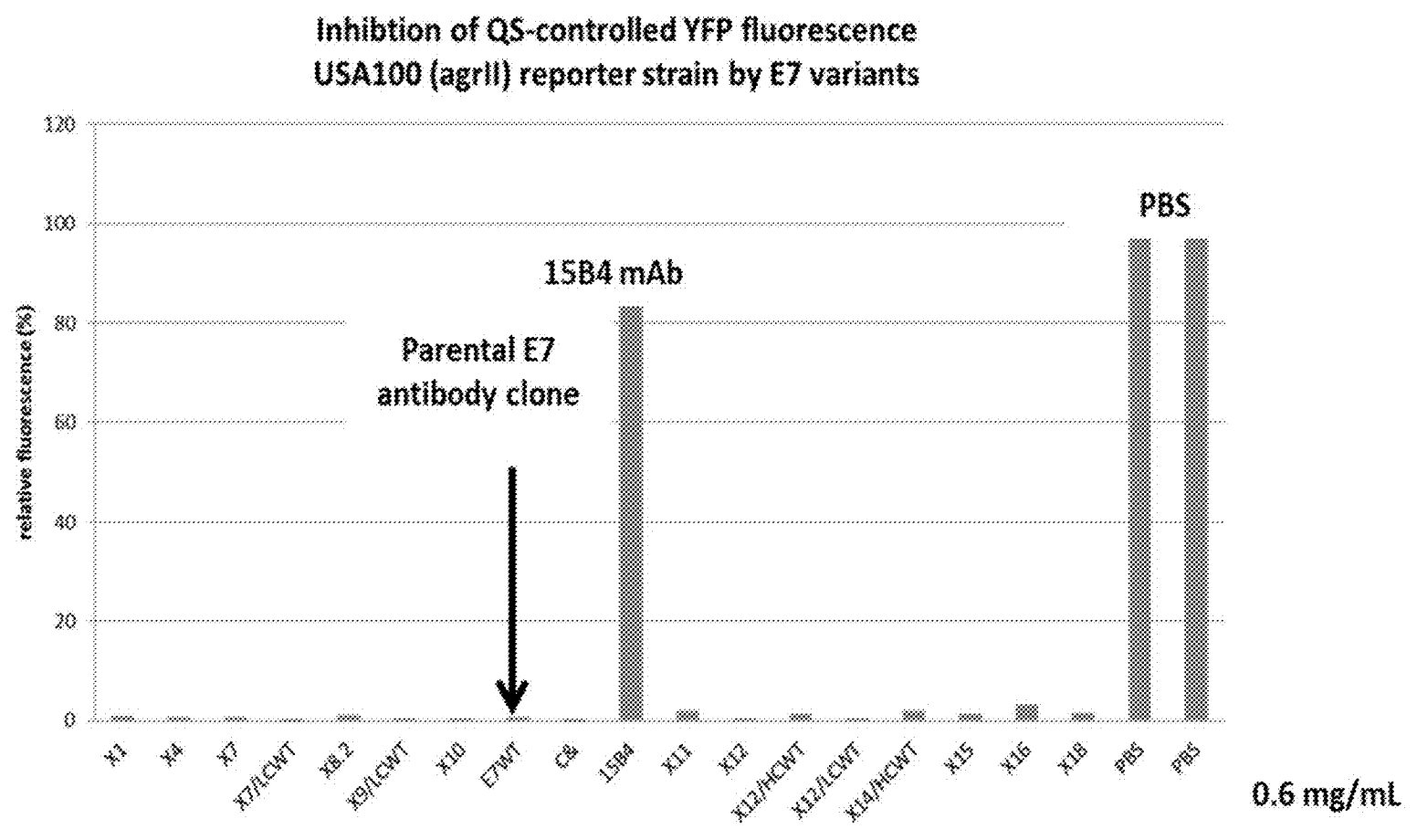

FIG. 2 shows inhibition of AIP2 mediated QS in SA502A (agrII) by engineered E7 variant IgG s.

FIG. 5 shows in vivo profiling of anti-AIP antibody efficacy.

DETAILED DESCRIPTION

Figure 1:
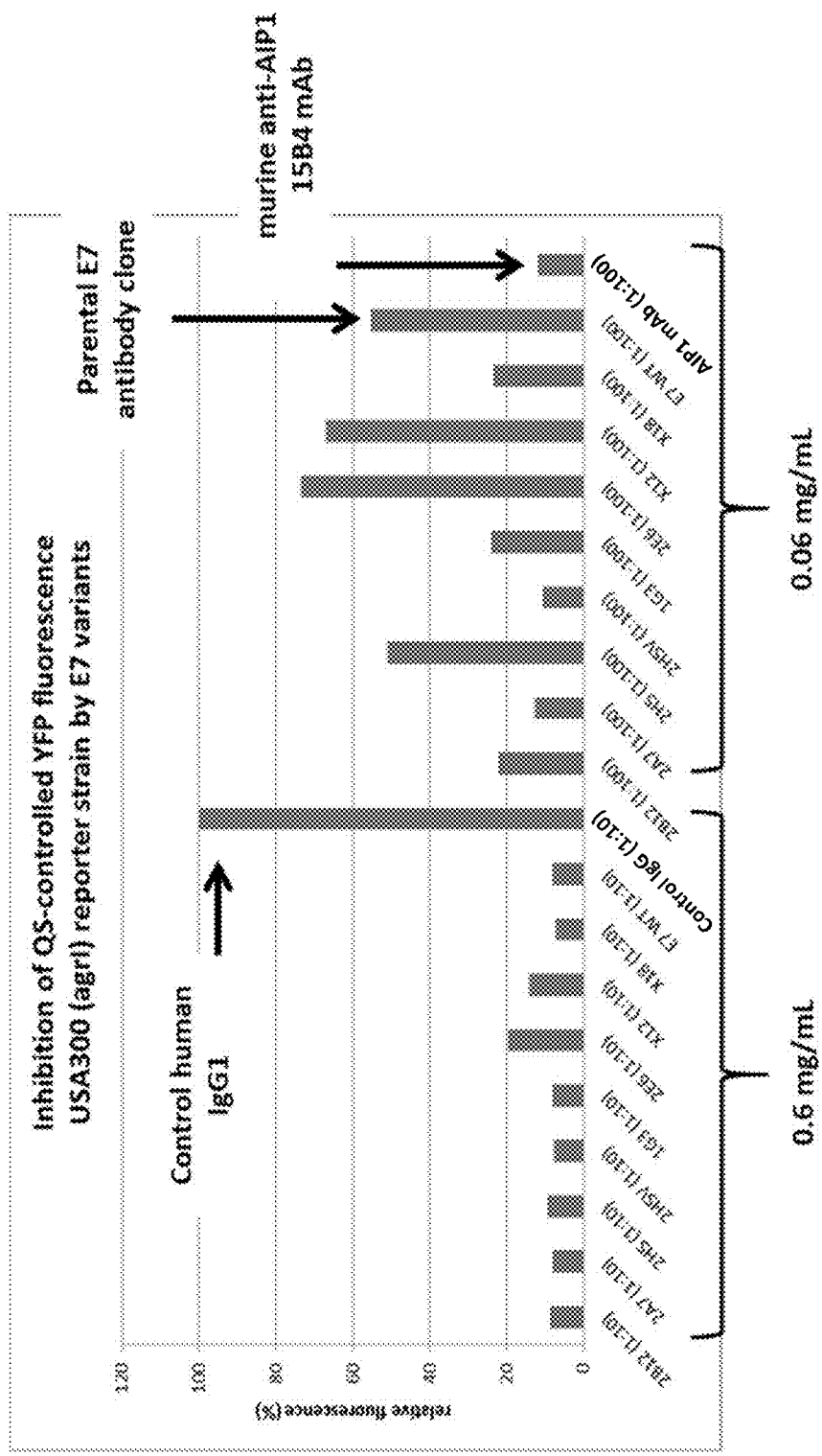
FIG. 1 shows inhibition of AIP1 mediated QS in USA300 (agrI) by engineered E7 variant IgG s.

The present disclosure provides anti-AIP2 antibody variant clones, and their antigen binding proteins thereof, that are improved for inhibiting pathogenic bacterial quorum sensing (QS) compared to the wild type anti-AIP2 antibody E7 from which the variant clones are derived. In one embodiment, the variant anti-AIP2 antibodies and antigen binding proteins thereof bind autoinducer peptides produced by *Staphylococcus aureus* to interfere quorum sensing signaling. In an in vivo model, animals pre-treated with the variant anti-AIP2 antibodies provided were better protected against a lethal *Staphylococcus aureus* challenge compared to animals pre-treated with wild type anti-AIP2 antibody E7.

An antibody (E7) disclosed in U.S. patent application Ser. No. 14/062,774 filed 24 Oct. 2013, now issued U.S. Pat. No. 8,859,740, (both disclosures are incorporated by reference herein in their entireties) as wild type SEQ ID NO: 1 for the heavy chain and SEQ ID NO: 2 for the light chain demonstrated improved binding characteristics when modified in both its heavy chain and light chain sequences. Therefore, the present disclosure provides a fully human antibody of an IgG class that binds to an AIP2 epitope, comprising an antibody selected from the group consisting of 1G3, 2A7, 2B12, 2(E)6, 2H5, X18, X12 and 2H5 variant (also called 2H5v). In one embodiment, the heavy chain/light chain sequence sets include: SEQ ID NO: 3 for heavy chain/SEQ ID NO: 2 for the light chain for 1G3; SEQ ID NO:4 for heavy chain/SEQ ID NO:2 for the light chain for 2A7; SEQ ID NO:5 for heavy chain/SEQ ID NO:2 for the light chain for 2B12; SEQ ID NO:6 for heavy chain/SEQ ID NO:2 for the light chain for 2(E)6; SEQ ID NO:7 for heavy chain/SEQ ID NO:2 for the light chain for 2H5; SEQ ID NO:8 for heavy chain/SEQ ID NO:9 for the light chain for X18; SEQ ID NO: 10 for heavy chain/SEQ ID NO:11 for the light chain for X12; and SEQ ID NO: 12 for heavy chain/SEQ ID NO:9 for the light chain for 2H5V.

The present disclosure provides a Fab fully human antibody fragment that binds to an AIP2 epitope, selected from the group consisting of 1G3, 2A7, 2B12, 2H5, X18, X12 and 2H5 variant. In one embodiment, the heavy chain/light chain sequence sets include: SEQ ID NO: 3 for heavy chain/SEQ ID NO: 2 for the light chain for 1G3; SEQ ID NO:4 for heavy chain/SEQ ID NO:2 for the light chain for 2A7; SEQ ID NO:5 for heavy chain/SEQ ID NO:2 for the light chain for 2B12; SEQ ID NO:6 for heavy chain/SEQ ID NO:2 for the light chain for 2(E)6; SEQ ID NO:7 for heavy chain/SEQ ID NO:2 for the light chain for 2H5; SEQ ID NO:8 for heavy chain/SEQ ID NO:9 for the light chain for X18; SEQ ID NO:10 for heavy chain/SEQ ID NO:11 for the light chain for X12; and SEQ ID NO: 12 for heavy chain/SEQ ID NO:9 for the light chain for 2H5V.

The present disclosure provides a single chain human antibody that binds to an AIP2 epitope, selected from the group consisting of 1G3, 2A7, 2B12, 2H5, X18, X12 and 2H5 variant. In one embodiment, the heavy chain/light chain sequence sets include: SEQ ID NO: 3 for heavy chain/SEQ ID NO: 2 for the light chain for 1G3; SEQ ID NO:4 for heavy chain/SEQ ID NO:2 for the light chain for 2A7; SEQ ID NO:5 for heavy chain/SEQ ID NO:2 for the light chain for 2B12; SEQ ID NO:6 for heavy chain/SEQ ID NO:2 for the light chain for 2(E)6; SEQ ID NO:7 for heavy chain/SEQ ID NO:2 for the light chain for 2H5; SEQ ID NO:8 for heavy chain/SEQ ID NO:9 for the light chain for X18; SEQ ID NO: 10 for heavy chain/SEQ ID NO:11 for the light chain for X12; and SEQ ID NO: 12 for heavy chain/SEQ ID NO:9 for the light chain for 2H5V.

Definitions

The term "isolated" refers to a protein or polynucleotide (e.g., an antibody or an antigen binding portion thereof) that is substantially free of other cellular material. A protein may be rendered substantially free of naturally associated components (or components associated with the cellular expression system used to produce the antibody) by isolation, using protein purification techniques well known in the art. In one embodiment, the anti-AIP2 antibodies or antigen binding portions thereof, of the present disclosure are isolated.

The terms "anti-AIP2 antibody" and "an antibody that binds to AIP2" and related terms as used herein refer to an antibody that is capable of binding AIP2 with sufficient affinity such that the antibody is useful as a diagnostic and/or therapeutic agent in targeting AIP2, including human AIP2.

An "epitope" and related terms as used herein refers to a portion of a molecule that is bound by an antigen binding protein (e.g., by an antibody or an antigen binding portion thereof). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein). Generally the variable regions, particularly the CDRs, of an antibody interact with the epitope.

The terms "specific binding", "specifically binds" or "specifically binding" and other related terms, as used herein in the context of an antibody, refer to non-covalent or covalent preferential binding of an antibody to an antigen relative to other molecules or moieties (e.g., an antibody specifically binds to a particular antigen relative to other available antigens). In one embodiment, an antibody specifically binds to an antigen (e.g., AIP2) if it binds to the antigen with a dissociation constant $K_d$ of $10^{-5}$ M or less, or $10^{-6}$ M or less, or $10^{-7}$ M or less, or $10^{-8}$ M or less, or $10^{-9}$ M or less, or $10^{-10}$ M or less.

In one embodiment, a dissociation constant ($K_d$) can be measured using a BIACORE surface plasmon resonance (SPR) assay. Surface plasmon resonance refers to an optical phenomenon that allows for the analysis of real-time interactions by detection of alterations in protein concentrations within a biosensor matrix, for example using the BIACORE system (Biacore Life Sciences division of GE Healthcare, Piscataway, N.J.).

An "antigen binding protein" and related terms used herein is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, Proteins: Structure, Function, and Bioinformatics, Volume 53, Issue 1:121-129; Roque et al., 2004, Biotechnol. Prog. 20:639-654. In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

The variable regions of naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, 5$^{th}$ Ed., US Dept. of Health and Human Services, PHS, NIH, NIH Publication no. 91-3242, 1991. Other numbering systems for the amino acids in immunoglobulin chains include IMGT® (international ImMunoGeneTics information system; Lefranc et al, *Dev. Comp. Immunol.* 29:185-203; 2005) and AHo (Honegger and Pluckthun, *J. Mol. Biol.* 309(3):657-670; 2001).

Antibodies can be obtained from sources such as serum or plasma that contain immunoglobulins having varied antigenic specificity. If such antibodies are subjected to affinity purification, they can be enriched for a particular antigenic specificity. Such enriched preparations of antibodies usually are made of less than about 10% antibody having specific binding activity for the particular antigen. Subjecting these preparations to several rounds of affinity purification can increase the proportion of antibody having specific binding activity for the antigen. Antibodies prepared in this manner are often referred to as "monospecific." Monospecific antibody preparations can be made up of about 10%, 20%, 30%, 40%, 50%, 60%, 70%, 75%, 80%, 85%, 90%, 95%, 97%, 99%, or 99.9% antibody having specific binding activity for the particular antigen.

An "antibody" and "antibodies" and related terms used herein refers to an intact immunoglobulin or to an antigen binding portion thereof that competes with the intact antibody for specific binding, unless otherwise specified. Antigen binding portions may be produced by recombinant DNA techniques or by enzymatic or chemical cleavage of intact antibodies. Antigen binding portions include, inter alia, Fab, Fab', F(ab')$_2$, Fv, domain antibodies (dAbs), and complementarity determining region (CDR) fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

A Fab fragment is a monovalent fragment having the $V_L$, $V_H$, $C_L$ and $C_{H1}$ domains; a F(ab')$_2$ fragment is a bivalent fragment having two Fab fragments linked by a disulfide bridge at the hinge region; a Fd fragment has the $V_H$ and $C_{H1}$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634; 6,696,245, US App. Pub. 20/0202512; 2004/0202995; 2004/0038291; 2004/0009507; 2003/0039958, and Ward et al., Nature 341: 544-546, 1989).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., 1988, Science 242:423-26 and Huston et al., 1988, Proc. Natl. Acad. Sci. USA 85:5879-83). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, Proc. Natl. Acad. Sci. USA 90:6444-48, and Poljak et al., 1994, Structure 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Complementarity determining regions (CDRs) and framework regions (FR) of a given antibody may be identified using the system described by Kabat et al. supra; Lefranc et al., supra and/or Honegger and Pluckthun, supra. One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

An "antibody fragment". "antibody portion", "antigen-binding fragment of an antibody", or "antigen-binding portion of an antibody" and other related terms used herein refer to a molecule other than an intact antibody that comprises a portion of an intact antibody that binds the antigen to which the intact antibody binds. Examples of antibody fragments include, but are not limited to, Fv, Fab, Fab', Fab'-SH, F(ab')$_2$; Fd; and Fv fragments, as well as dAb; diabodies; linear antibodies; single-chain antibody molecules (e.g. scFv); polypeptides that contain at least a portion of an antibody that is sufficient to confer specific antigen binding to the polypeptide. Antigen binding portions of an antibody may be produced by recombinant DNA techniques or by enzymatic or chemical cleavage of intact antibodies. Antigen binding portions include, inter alia, Fab, Fab', F(ab')2, Fv, domain antibodies (dAbs), and complementarity determining region (CDR) fragments, chimeric antibodies, diabodies, triabodies, tetrabodies, and polypeptides that contain at least a portion of an immunoglobulin that is sufficient to confer antigen binding properties to the antibody fragment.

An "antigen binding domain." "antigen binding region," or "antigen binding site" and other related terms used herein is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

The term "human antibody" includes all antibodies that have one or more variable and constant regions derived from human immunoglobulin sequences. In one embodiment, all of the variable and constant domains are derived from human immunoglobulin sequences (e.g., a fully human antibody). These antibodies may be prepared in a variety of ways, examples of which are described below, including through recombinant methodologies or through immunization with an antigen of interest of a mouse that is genetically modified to express antibodies derived from human heavy and/or light chain-encoding genes.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" and related terms used herein refers to an antibody that contains one or more regions from one antibody and one or more regions from one or more other antibodies. In one embodiment, one or more of the CDRs are derived from a human anti-AIP2 antibody. In another embodiment, all of the CDRs are derived from a human anti-AIP2 antibody. In another embodiment, the CDRs from more than one human anti-AIP2 antibodies are mixed and matched in a chimeric antibody. For instance, a chimeric antibody may comprise a CDR1 from the light chain of a first human anti-AIP2 antibody, a CDR2 and a CDR3 from the light chain of a second human anti-AIP2 antibody, and the CDRs from the heavy chain from a third anti-AIP2 antibody. One skilled in the art will appreciate that other combinations are possible.

Further, the framework regions may be derived from one of the same anti-AIP2 antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody (-ies) from another species or belonging to another antibody class or subclass. Also included are fragments of such antibodies that exhibit the desired biological activity (i.e., the ability to specifically bind AIP2).

The term "labeled antibody" or related terms as used herein refers to antibodies and their antigen binding portions thereof that are unlabeled or joined to a detectable label or moiety for detection in a format such as radioactive, colorimetric, antigenic, enzymatic molecule, a detectable bead (such as a magnetic or electrodense (e.g., gold) bead), or biotin or streptavidin. A variety of labels can be employed, including, but not limited to, radionuclides, fluorescers, enzymes, enzyme substrates, enzyme cofactors, enzyme inhibitors and ligands (e.g., biotin, haptens).

Numerous appropriate immunoassays are known to the skilled artisan (see, for example, U.S. Pat. Nos. 3,817,827; 3,850,752; 3,901,654; and 4,098,876). When unlabeled, the antibodies and their antigen binding portions thereof can be used in assays, such as agglutination assays. Unlabeled antibodies and their antigen binding portions thereof can also be used in combination with another (one or more) suitable reagent which can be used to detect the binding polypeptide, such as a labeled antibody reactive with the binding polypeptide or other suitable reagent (e.g., labeled protein A).

In one embodiment, the antibodies and their antigen binding portions thereof can be conjugated to an enzyme for use in an enzyme immunoassays. When a sample comprising a AIP2 protein is combined with at least one of the subject antibody, binding occurs between the antibody and the AIP2 protein. In one embodiment, a sample containing cells expressing an AIP2 protein (e.g., endothelial cells) is combined with at least one of the subject antibodies, and binding occurs between the antibody(ies) and the cells bearing a AIP2 protein. These bound cells can be separated from unbound cells and the presence of the antibody-enzyme conjugate specifically bound to the cells can be determined, for example, by contacting the sample with a substrate of the enzyme which produces a color or other detectable change when acted on by the enzyme. In another embodiment, at least one antibody can be unlabeled, and a second, labeled polypeptide (e.g., an antibody) can be added which recognizes the subject binding polypeptide. In one embodiment, labeled antibodies (and labeled antigen binding portions thereof) can be used in a diagnostic assays which involves detecting the formation of a complex resulting from the binding of a labeled antibody to the target antigen (e.g., ALP protein).

The terms "nucleic acid", "polynucleotide" and "oligonucleotide" and other related terms used herein are used interchangeably and refers to polymers of nucleotides. Nucleic acids include naturally-occurring, recombinant and chemically-synthesized forms. Nucleic acids include DNA molecules (cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. Nucleic acid molecule can be single-stranded or double-stranded. In one embodiment, the nucleic acid molecules of the disclosure comprise a contiguous open reading frame encoding an antibody, or a fragment or scFv, derivative, mutein, or variant thereof.

The terms "peptide", "polypeptide" and "protein" and other related terms used herein are used interchangeably and refer to a polymer of amino acids and are not limited to any particular length. Polypeptides comprise natural and non-natural amino acids. Polypeptides can be naturally-occurring or recombinant or chemically-synthesized forms. These terms encompass native and artificial proteins, protein fragments and polypeptide analogs (such as muteins, variants, chimeric proteins and fusion proteins) of a protein sequence as well as post-translationally, or otherwise covalently or non-covalently, modified proteins. A peptide, polypeptide, or protein may be monomeric or polymeric. Polypeptides includes antibodies, portions of antibodies, antibody chains, scFv and chimeric antigen receptor constructs.

The "percent identity" or "percent homology" and related terms used herein refers to a quantitative measurement of the similarity between two polypeptide or between two polynucleotide sequences. The percent identity between two polypeptide sequences is a function of the number of identical amino acids at aligned positions that are shared between the two polypeptide sequences, taking into account the number of gaps, and the length of each gap, which may need to be introduced to optimize alignment of the two polypeptide sequences. In a similar manner, the percent identity between two polynucleotide sequences is a function of the number of identical nucleotides at aligned positions that are shared between the two polynucleotide sequences, taking into account the number of gaps, and the length of each gap, which may need to be introduced to optimize alignment of the two polynucleotide sequences. A comparison of the sequences and determination of the percent identity between two polypeptide sequences, or between two polynucleotide sequences, may be accomplished using a mathematical algorithm. For example, the "percent identity" or "percent homology" of two polypeptide or two polynucleotide sequences may be determined by comparing the sequences using the GAP computer program (a part of the GCG Wisconsin Package, version 10.3 (Accelrys, San Diego, Calif.)) using its default parameters.

In one embodiment, the amino acid sequence of an anti-AIP2 antibody may be similar but not identical to any of the amino acid sequences of the anti-AIP2 antibodies described herein. The similar anti-AIP2 antibody can be at least 95%, or at or at least 96% identical, or at least 97% identical, or at least 98% identical, or at least 99% identical, to any of the anti-AIP2 antibodies described herein. In one embodiment, similar anti-AIP2 antibodies can contain amino acid substitutions within a heavy and/or light chain. In one embodiment, the amino acid substitutions comprise one or more conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference in its entirety. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine.

A "vector" and related terms used herein refers to a nucleic acid molecule (e.g., DNA or RNA) which can be operably linked to foreign genetic material (e.g., nucleic acid transgene). Vectors can be used as a vehicle to introduce foreign genetic material into a cell (e.g., host cell). Vectors can include at least one restriction endonuclease recognition sequence for insertion of the transgene into the vector. Vectors can include at least one gene sequence that confers antibiotic resistance or selectable characteristic to aid in selection of host cells that harbor a vector-transgene construct. Vectors can be single-stranded or double-stranded nucleic acid molecules. Vectors can be linear or circular nucleic acid molecules. One type of vector is a "plasmid," which refers to a linear or circular double stranded extrachromosomal DNA molecule which can be linked to a transgene, and is capable of replicating in a host cell, and transcribing and/or translating the transgene. A viral vector typically contains viral RNA or DNA backbone sequences which can be linked to the transgene. The viral backbone sequences can be modified to disable infection but retain insertion of the viral backbone and the co-linked transgene into a host cell genome. Examples of viral vectors include retroviral, lentiviral, adenoviral and adeno-associated vectors. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can contain one or more regulatory sequences, such as inducible and/or constitutive promoters and enhancers. Expression vectors can include ribosomal binding sites and/or polyadenylation sites. Regulatory sequences direct transcription, or transcription and translation, of a transgene linked to the expression vector which is transduced into a host cell. The regulatory sequence(s) can control the level, timing and/or location of expression of the transgene. The regulatory sequence can, for example, exert its effects directly on the transgene, or through the action of one or more other molecules (e.g., polypeptides that bind to the regulatory sequence and/or the nucleic acid). Regulatory sequences can be part of a vector. Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-3606.

A transgene is "operably linked" to a vector when there is linkage between the transgene and the vector to permit functioning or expression of the transgene sequences contained in the vector. In one embodiment, a transgene is "operably linked" to a regulatory sequence when the regulatory sequence affects the expression (e.g., the level, timing, or location of expression) of the transgene.

The terms "transfected" or "transformed" or "transduced" or other related terms used herein refer to a process by which exogenous nucleic acid (e.g., transgene) is transferred or introduced into a host cell. A "transfected" or "transformed" or "transduced" host cell is one which has been transfected, transformed or transduced with exogenous nucleic acid (transgene). The host cell includes the primary subject cell and its progeny.

A "host cell" or "or a population of host cells" refers to a cell (or a population thereof) into which foreign (exogenous or transgene) nucleic acids have been introduced. The foreign nucleic acids can include an expression vector operably linked to a transgene, and the host cell can be used to express the nucleic acid and/or polypeptide encoded by the foreign nucleic acid (transgene). A host cell (or a population thereof) can be a cultured cell or can be extracted from a subject. The host cell (or a population thereof) includes the primary subject cell and its progeny without any regard for the number of passages. Progeny cells may or may not harbor identical genetic material compared to the parent cell. Host cells encompass progeny cells. In one embodiment, a host cell describes any cell (including its progeny) that has been modified, transfected, transduced, transformed, and/or manipulated in any way to express an anti-AIP2 antibody, as disclosed herein. In one example, the host cell (or population thereof) can be introduced with an expression vector operably linked to a nucleic acid encoding the anti-AIP2 antibody, or an antigen binding portion thereof, described herein. Host cells and populations thereof can harbor an expression vector that is stably integrated into the host's genome, or can harbor an extrachromosomal expression vector. In one embodiment, host cells and populations thereof can harbor an extrachromosomal vector that is present after several cell divisions or is present transiently and is lost after several cell divisions.

A host cell can be a prokaryote, for example, E. coli, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. In one embodiment, a host cell can be introduced with an expression vector operably linked to a nucleic acid encoding an anti-AIP2 antibody thereby generating a transfected/transformed host cell which is cultured under conditions suitable for expression of the anti-AIP2 antibody by the transfected/transformed host cell, and optionally recovering the anti-AIP2 antibody from the transfected/transformed host cells or from the culture medium. Examples of host cells include the COS-7 line of monkey kidney cells (ATCC CRL 1651) (see Gluzman et al., 1981, Cell 23: 175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, Cytotechnology 28:31) or CHO strain DX-B11, which is deficient in DHFR (see Urlaub et al., 1980, Proc. Natl. Acad. Sci. USA 77:4216-20), HeLa cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293,293 EBNA or MSR 293, human epidermal A431 cells, human Colo 205 cells, other transformed primate cell lines, normal diploid cells, cell strains derived from in vitro culture of primary tissue, primary explants, HL-60, U937, HaK or Jurkat cells. In one embodiment, host cells include lymphoid cells such as Y0, NS0 or Sp20. In one embodiment, a host cell is a mammalian host cell, but is not a human host cell. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Polypeptides of the present disclosure (e.g., antibodies and antigen binding proteins) can be produced using any standard methods known in the art. In one example, the polypeptides are produced by recombinant DNA methods by inserting a nucleic acid sequence (e.g., DNA) encoding the polypeptide into a recombinant expression vector and expressing the DNA sequence under conditions promoting expression.

General techniques for recombinant nucleic acid manipulations are described for example in Sambrook et al., in Molecular Cloning: A Laboratory Manual, Vols. 1-3, Cold Spring Harbor Laboratory Press, 2 ed., 1989, or F. Ausubel et al., in Current Protocols in Molecular Biology (Green Publishing and Wiley-Interscience: New York, 1987) and periodic updates, herein incorporated by reference in their entireties. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants is additionally incorporated.

The recombinant DNA can also encode any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in Cloning Vectors: A Laboratory Manual, (Elsevier, N.Y., 1985).

The expression vector construct can be introduced into the host cell using a method appropriate for the host cell. A variety of methods for introducing nucleic acids into host cells are known in the art, including, but not limited to, electroporation; transfection employing calcium chloride, rubidium chloride, calcium phosphate. DEAE-dextran, or other substances; viral transfection; non-viral transfection; microprojectile bombardment; lipofection; and infection (e.g., where the vector is an infectious agent). Suitable host cells include prokaryotes, yeast, mammalian cells, or bacterial cells.

Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (Bio/Technology, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

Proteins disclosed herein can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

Nucleic acids encoding any of the various polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., Proc. Natl. Acad. Sci. USA. 2003 100(2):438-42; Sinclair et al. Protein Expr. Purif. 2002 (1):96-105; Connell N D. Curr. Opin. Biotechnol. 2001 12(5):446-9; Makrides et al. Microbiol. Rev. 1996 60(3):512-38; and Sharp et al. Yeast. 1991 7(7):657-78.

Anti-AIP2 antibodies and derivatives described herein can also be produced by chemical synthesis (e.g., by the methods described in Solid Phase Peptide Synthesis, 2nd ed., 1984, The Pierce Chemical Co., Rockford. Ill.). Modifications to the protein can also be produced by chemical synthesis.

Anti-AIP2 antibodies and derivatives described herein can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified anti-AIP2 antibodies and derivatives described herein are preferably at least 85% pure, more preferably at least 95% pure, and most preferably at least 98% pure. Regardless of the exact numerical value of the purity, the polypeptide is sufficiently pure for use as a pharmaceutical product.

In certain embodiments, the anti-AIP2 antibodies and derivatives described herein can further comprise post-translational modifications. Exemplary post-translational protein modifications include phosphorylation, acetylation, methylation. ADP-ribosylation, ubiquitination, glycosylation, carbonylation, sumoylation, biotinylation or addition of a polypeptide side chain or of a hydrophobic group. As a result, the modified polypeptides may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogenicity of the protein. See Raju et al. Biochemistry. 2001 31; 40(30):8868-76.

In one embodiment, the anti-AIP2 antibodies and derivatives described herein can be modified to become soluble polypeptides which comprises linking the anti-AIP2 antibodies or their derivatives to non-proteinaceous polymers. In one embodiment, the non-proteinaceous polymer comprises polyethylene glycol ("PEG"), polypropylene glycol, or polyoxyalkylenes, in the manner as set forth in U.S. Pat. No. 4,640,835; 4,496,689; 4,301,144; 4,670,417; 4,791,192 or 4,179,337.

PEG is a water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: X—O$(CH_2CH_2O)_n$—$CH_2CH_2OH$ (1), where n is 20 to 2300 and X is H or a terminal modification. e.g., a $C_{1-4}$ alkyl. In one embodiment, the PEG terminates on one end with hydroxy or methoxy, i.e., X is H or $CH_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462. One form of PEGs includes two PEG side-chains (PEG2) linked via the primary amino groups of a lysine (Monfardini et al., Bioconjugate Chem. 6 (1995) 62-69).

The serum clearance rate of PEG-modified polypeptide may be decreased by about 10%, 20%, 30%, 40%, 50%, 60%, 70%, 80%, or even 90%, relative to the clearance rate of the unmodified AIP2 binding polypeptides. The PEG-modified polypeptide may have a half-life (tin) which is enhanced relative to the half-life of the unmodified polypeptide. The half-life of PEG-modified polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified AIP2 binding polypeptide. In some embodiments, the protein half-life is determined in vitro, such as in a buffered saline solution or in serum. In other embodiments, the protein half-life is an in vivo half life, such as the half-life of the protein in the serum or other bodily fluid of an animal.

The present disclosure provides method for preventing or treating a *Staphylococcus aureus* infection comprising administering to a subject a therapeutic composition comprising an anti-AIP2 polypeptide. Techniques and dosages for administration vary depending on the type of specific polypeptide and the specific condition being treated but can be readily determined by the skilled artisan. In general, regulatory agencies require that a polypeptide to be used as a therapeutic is formulated so as to have acceptably low levels of pyrogens. Accordingly, therapeutic formulations will generally be distinguished from other formulations in that they are substantially pyrogen-free, or at least contain no more than acceptable levels of pyrogen as determined by the appropriate regulatory agency (e.g., FDA).

Therapeutic compositions comprising a variant anti-AIP2 antibody may be administered with a pharmaceutically acceptable diluent, carrier, or excipient, in unit dosage form. Administration may be parenteral (e.g., intravenous, subcutaneous), oral, or topical, as non-limiting examples. In addition, any gene therapy technique, using nucleic acids encoding the AIP2-binding polypeptides, may be employed, such as naked DNA delivery, recombinant genes and vectors, cell-based delivery, including ex vivo manipulation of patients' cells, and the like.

Therapeutic compositions can be in the form of a pill, tablet, capsule, liquid, or sustained release tablet for oral administration; or a liquid for intravenous, subcutaneous or parenteral administration; gel, lotion, ointment, cream, or a polymer or other sustained release vehicle for local administration.

Methods for making therapeutic compositions are well known in the art and are found, for example, in "Remington: The Science and Practice of Pharmacy" (20th ed., ed. A. R. Gennaro A R., 2000, Lippincott Williams & Wilkins. Philadelphia. Pa.). Therapeutic compositions can be formulated for parenteral administration may, and can for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the anti-AIP2 antibody (or antigen binding protein thereof). Nanoparticulate formulations (e.g., biodegradable nanoparticles, solid lipid nanoparticles, liposomes) may be used to control the biodistribution of the anti-AIP2 antibody (or antigen binding protein thereof). Other potentially useful parenteral delivery systems include ethylene-vinyl acetate copolymer particles, osmotic pumps, implantable infusion systems, and liposomes. The concentration of the anti-AIP2 antibody (or antigen binding protein thereof) in the formulation varies depending upon a number of factors, including the dosage of the drug to be administered, and the route of administration.

The anti-AIP2 antibody (or antigen binding protein thereof) may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. In one example, the anti-AIP2 antibody (or antigen binding protein thereof) is formulated in the presence of sodium acetate to increase thermal stability.

The anti-AIP2 antibody (or antigen binding protein thereof) may be formulated for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

The term "effective amount" as used herein, refers to that amount of a variant antibody or an antigen binding portion thereof that binds AIP2, that when administered to a subject, is sufficient to effect a measurable improvement or prevention of a disease or disorder associated with AIP2 signaling. Therapeutically effective amounts of antibodies provided herein, when used alone or in combination, will vary depending upon the relative activity of the antibodies and combinations (e.g., in inhibiting cell growth) and depending upon the subject and disease condition being treated, the weight and age and sex of the subject, the severity of the disease condition in the subject, the manner of administration and the like, which can readily be determined by one of ordinary skill in the art.

In one embodiment, a therapeutically effective amount will depend on certain aspects of the subject to be treated and the disorder to be treated, and may be ascertained by one skilled in the art using known techniques. In general, the polypeptide is administered at about 0.01 g/kg to about 50 mg/kg per day, preferably 0.01 mg/kg to about 30 mg/kg per day, most preferably 0.1 mg/kg to about 20 mg/kg per day. The polypeptide may be administered daily (e.g., once, twice, three times, or four times daily) or preferably less frequently (e.g., weekly, every two weeks, every three weeks, monthly, or quarterly). In addition, as is known in the art, adjustments for age as well as the body weight, general health, sex, diet, time of administration, drug interaction, and the severity of the disease may be necessary.

The present disclosure is based on quorum quenching (QQ). The QQ approach modulates the global virulence of the invading pathogens, thus allowing the bacteria to be cleared by the host's immune system. The original fully human anti-AIP2 antibody, E7, is also cross-reactive with AIP1 and AIP4. The disclosed variant antibodies have demonstrated improved biochemical and biophysical properties, and complete protection against a lethal CA-MRSA USA300 infection.

EXAMPLES

The following examples are meant to be illustrative and can be used to further understand embodiments of the present disclosure and should not be construed as limiting the scope of the present teachings in any way.

Example 1

Quorum-Sensing Controlled YFP Reporter Strain agr Group I:

The results of a quorum sensing-controlled (QS-controlled) YFP reporter assay for anti-AIP1 activity is shown in FIG. 1. The results show that variant clones 2A7, 2H5v and X18 showed improvement in suppressing YFP signal in agr1 strain, relative to parental E7, and variant clones 2E6 and X12, and comparable to anti-AIP1 mAb (15B4) that was isolated from hybridoma by immunization of mouse with AIP1. The variant antibody 2H5v is combination of 2H5 HC (original LC is E7) and X18LC. IgG1 antibody for 2A7, 2H5v, 1G3 together with parental E7 and variant X18 were expressed at 30 to 100 mg level for animal studies.

Briefly, the *S. aureus* YFP reporter strain carrying the plasmid pDB59 (Malone et al., 2009 Journal of Microbial Methods 77:251-260) representing agr group I (USA300 LAC) was grown overnight in tryptic soy broth supplemented with chloramphenicol at 10 µg/mL at 37° C. with shaking. The pDB59 plasmid contained an agr P3-YFP promoter fusion construct. For antibody-mediated QS inhibition evaluation, cultures were diluted 100-fold into fresh media, incubated for 1 h at 37° C., and 180 µL were dispensed into wells of a 96-well microtiter plate. The 8 mAbs of interest (1G3, 2A7, 2B12, 2(E)6, 2H5, X18, X12 and 2H5v) were diluted to a working concentration of 6 mg/mL in PBS, and diluted 1:10. The various variant anti-AIP2 and control antibodies were tested at 0.6 mg/mL or 0.06 mg/mL as indicated along the x-axis of FIG. 1. 20 µL of each antibody dilution was added to the reporter cultures in the microtiter plates in triplicate, resulting in an additional 10-fold dilution. Control antibodies included the 3 parental mAbs (E7, C7 and D3), murine anti-AIP1 mAb (15B4), and human IgG. Plates were incubated for 24 h at 37° C. with shaking at 200 rpm. Absorbance (OD 600) and fluorescence were measured using an excitation wavelength of 485 nm and an emission wavelength of 530 nm.

Quorum-Sensing Controlled YFP Reporter Strain agr Group II:

The results of a quorum sensing-controlled (QS-controlled) YFP reporter assay for anti AIP2 activity is shown in FIG. 2. The results show that all anti-AIP2 antibody clones maintained the ability to suppress YFP signal in agr2 strain.

Briefly, the *S. aureus* YFP reporter strain carrying the plasmid pDB59 representing agr group II (SA502A) was grown overnight in tryptic soy broth supplemented with chloramphenicol at 10 µg/mL at 37° C. with shaking. For antibody-mediated QS inhibition evaluation, cultures were diluted 100-fold into fresh media, incubated for 1 h at 37° C., and 180 µL were dispensed into wells of a 96-well microtiter plate. The 8 mAbs of interest were diluted to a working concentration of 6 mg/mL in PBS, and diluted 1:10. The various variant anti-AIP2 and control antibodies were tested at 0.6 mg/mL as indicated along the x-axis of FIG. 2. 20 µL of each antibody dilution was added to the reporter cultures in the microtiter plates in triplicate, resulting in an additional 10-fold dilution. Control antibodies included the 3 parental mAbs (E7, C7 and D3), murine anti-AIP1 mAb (15B4), and human IgG1. Plates were incubated for 24 h at 37° C. with shaking at 200 rpm. Absorbance (OD 600) and fluorescence were measured using an excitation wavelength of 485 nm and an emission wavelength of 530 nm.

Figure 3:
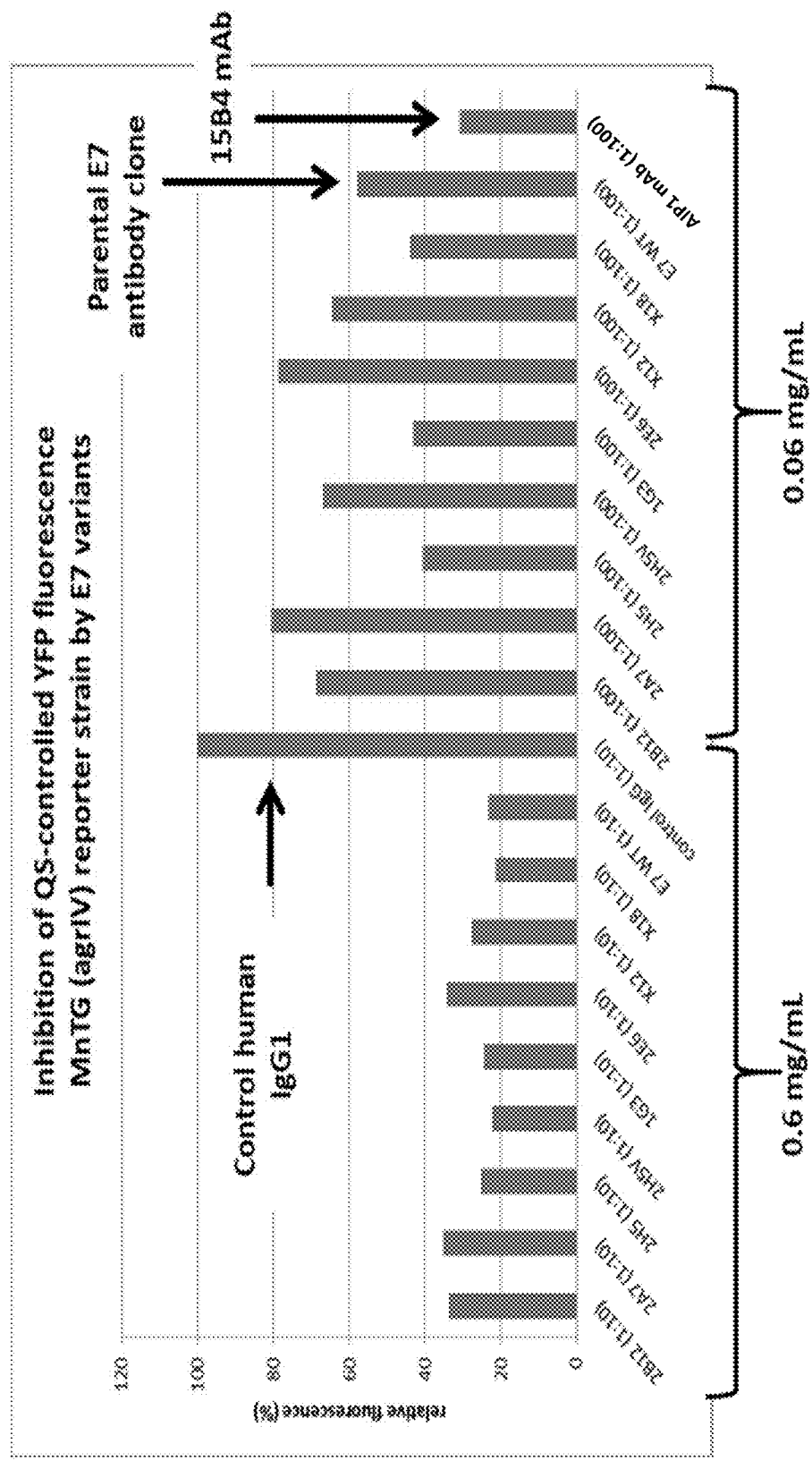
FIG. 3 shows inhibition of AIP4-mediated QS in MN EV (agrIV) by engineered E7 variant IgG s.

Quorum-Sensing Controlled YFP Reporter Strain agr Group IV:

The results of a a quorum sensing-controlled (QS-controlled) YFP reporter assay for anti-AIP4 activity is shown in FIG. 3. The results show that variant clones 2H5, 1G3 and X18 showed improvement in suppressing YFP signal in agr4 strain, relative to parental E7, and variant clones 2B12, 2A7, 2H5v, 2(E)6 and X12, but not as effective as murine anti-AIP1 mAb 15B4.

Briefly, the *S. aureus* YFP reporter strain carrying the plasmid pDB59 representing agr group IV (MN EV) was grown overnight in tryptic soy broth supplemented with chloramphenicol at 10 μg/mL at 37° C. with shaking. For antibody-mediated QS inhibition evaluation, cultures were diluted 100-fold into fresh media, incubated for 1 h at 37° C., and 180 μL were dispensed into wells of a 96-well microtiter plate. The 8 mAbs of interest were diluted to a working concentration of 6 mg/mL in PBS, and diluted 1:10. The various variant anti-AIP2 and control antibodies were tested at 0.6 mg/mL or 0.06 mg/mL as indicated along the x-axis of FIG. 3. 20 μL of each antibody dilution was added to the reporter cultures in the microtiter plates in triplicate, resulting in an additional 10-fold dilution. Control antibodies included the 3 parental mAbs (E7, C7 and D3), murine anti-AIP1 mAb (15B4), and human IgG. Plates were incubated for 24 h at 37° C. with shaking at 200 rpm. Absorbance (OD 600) and fluorescence were measured using an excitation wavelength of 485 nm and an emission wavelength of 530 nm.

In conclusion, we were able to identify potent AIP1-mediated quorum quenching variants of the fully human antibody E7. E7 is cross-reactive against AIP-2 and AIP-4.

Example 2

This example provides biophysical properties of the disclosed antibodies.

A differential scanning calorimetry (DSC) experiment was done on a MicroCal VP-DSC. AIP2-mAb samples were diluted to 1 mg/mL in PBS buffer and was degassed for 10 minutes before analysis. The reference cell was filled with PBS buffer. The sample was heated from 20° C. to 90° C. at a heating rate of 60° C./hour. The pre-scan was 15 minutes, the filtering period was 10 seconds, and the feedback mode/gain was set to passive. The midpoint of a thermal transition temperature (Tm, or thermal transition temperature) was obtained by analyzing the data using Origin 7 software.

TABLE 1

| Protein | Tm (° C.) |
| --- | --- |
| AIP2-E7 | 66 |
| AIP2-E7-2H5V | 66 |
| AIP2-E7-2A7 | 67 |
| AIP2-E7-1G3 | 66 |
| AIP2-E7-X18 | 65 |

Example 3

Binding Affinity Analysis Via Surface Plasmon Resonance

Binding affinity studies were conducted using surface plasmon resonance (SPR) analysis. Wild type anti-AIP2 antibody E7 was compared to variant clones X12 and X18 using standard methods using BiaCore T200 (GE Healthcare) and the results are listed in Table 2.

TABLE 2

| Anti-AIP2 antibodies | ka (1/Ms) | kd (1/s) | Rmax (RU) | KA (1/M) | KD (M) | Chi2 |
| --- | --- | --- | --- | --- | --- | --- |
| E7 (wt) | 5.01E5 | 0.027 | 54.2 | 1.85E7 | 5.39E−8 | 0.303 |
| 12 | 1.86E5 | 0.012 | 38.5 | 1.54E7 | 6.49E−8 | 0.175 |
| 18 | 5.7E5 | 0.02 | 75.6 | 2.85E7 | 3.5E−8 | 0.953 |

Example 4

Mouse: Challenge with agrI S. aureus Strain.

Figure 4:
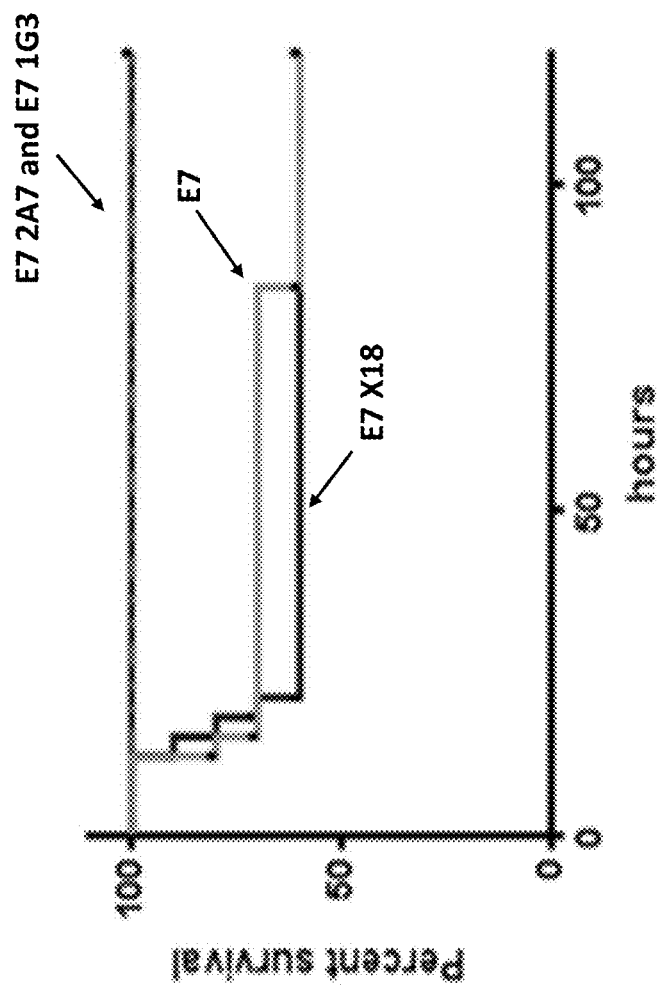
FIG. 4 shows data from 10 mice per group (*p=0.03 for E7 vs 2A7 or vs 1G3 as determined by Log Rank test).

Mice were pre-treated with 1 mg mAb AIP-E7 or variants E7X18, E72A7, E71G3. The mice were challenged 1 hour post-treatment with 2×10$^8$ (CA-MRSA USA300, agrI strain). Parental mAb E7 and derivative E7X18 had equal efficacy while E72A7 and E71 G3 provided significantly increased protection versus the parental E7 mAb (*p=0.03 for E7 vs 2A7 or vs 1G3) (FIG. 4). Parental mAbE7 and derivative E7X18 resulted in 60% survival whereas E72A7 and E71G3 provided 100% protection. Engineered variants E72A7 and E71G3 demonstrated complete protection against lethal invasive CA-MRSA USA300 (agrI) S. aureus disease at more than 100 hours post-challenge.

Example 4

Mouse: Challenge with agrIV S. aureus Strain.

Anti-AIP antibodies 2A7, 2H5V and control IgG1 were tested in an intravenous lethal invasive model of LAC USA300. In the IV challenge model, mice were immunized with 1 mg of antibodies via IP injection 2 hours prior to intravenous (IV) challenge with LAC USA300 (2×107 CFU/ml). Groups included 2H5V, 2A7, and human IgG control treated mice (FIG. 5). Group sizes were n=8 mice/group. Mice challenged in the IV model showed a delay in mortality following treatment with anti-AIP antibody 2A7 or 2H5V as compared to treatment with control human IgG.

Example 5

The wild type E7 and the most promising variant anti-AIP2 mAbs (see Table 1 in Example 2 above) were prepared and purified (e.g., isolated) by expression at large scale yielding 20 mg/L or more under standard transient expression conditions. Large scale shaker flask expression of the variant anti-AIP2 antibodies in CHO cells were performed using standard guidelines. Briefly, for transfection of desired volume of CHO-S cells were incubated in $CO_2$ incubator(s) to a cell density of about 1-2×10$^6$ cells/mL with viability no less than 90%. Expression vectors for heavy and light chain pairs were prepared using a commercial plasmid DNA extraction kit (Qiagen™ Maxi plasmid DNA extraction kit). DNA PEI complex for transfection was formed by mixing DNA and PEI (Polyethylenimine from Polyscience catalog No. 24765) at a ratio between 1:2-3 (weight/volume concentrations). CHO cells to DNA ratio was 10$^6$ cells per microgram DNA. DNA and PEI were complex was formed in OptiPRO™ media (Thermo Fisher Scientific) and added to the CHO cell cultures in the shaker flasks and incubated at 37° C. with rotation for overnight. On day 2 the cultures were expanded by doubling the culture media with CHO culturing media containing penicillin/streptomycin and placed in 30° C. incubator with rotation for 1 to 2 weeks depending on IgG titer and viability of the CHO cells. The variant anti-AIP2 antibodies were purified by batch type capturing of the molecules using commercial Protein A resins.

These data indicate commercial level expression levels of the anti-AIP2 antibodies are possible once stable expression cell lines have been generated. The disclosed variants possess outstanding biophysical properties, including virtually no tendency for aggregation (SEC data) and high thermostability (Tm≥65° C.; DSC data, see Table 1). Two of the variant anti-AIP2 antibodies (2A7 and 1G3) also provided complete protection against a lethal CA-MRSA USA300 infection (agrI strain, see FIG. 4).

TABLE 3 amino acid sequences of variant anti-AIP2 antibodies

| Anti-AIP2 antibody | Heavy chain variable domain region | Light chain variable domain region |
| --- | --- | --- |
| E7 wt | SEQ ID NO: 1<br>EVQLVQSGAEVKKPGASVRVSCK TSGYSFTSYDINWVRQTTGQLE WMGWVNPTSGSTGYAQKFQGR VTMTANTAINTAYMELRDLRSED TAVYFCVRDVPFDPWGQGTLVT VSS | SEQ ID NO: 2<br>QSVLTQPASVSGSPGQSITISCTGTS SDVGKYTFVSWYQQHPGKAPKV MVYEVNKRPLGVSPRFSGSKSGNT AYLTISGLQAEDEADYYCSSYTSSS TVVFGGGTKLTVL |
| 1G3 | SEQ ID NO: 3<br>QVQLVQSGSELKKPGASVKVSCK ASGYSFTTYGIHWVRQAPGQGLE WMGWLNTHTEHPTYAQGFTGRF VLSLDTSVSTAYLQITSLKAEDTA VYYCVRDDSFDPWGPGTLVTSS | SEQ ID NO: 2<br>QSVLTQPASVSGSPGQSITISCTGTS SDVGKYTFVSWYQQHPGKAPKV MVYEVNKRPLGVSPRFSGSKSGNT AYLTISGLQAEDEADYYCSSYTSSS TVVFGGGTKLTVL |
| 2A7 | SEQ ID NO: 4<br>QVQLVESGGGLVQPGRSLRLSCA ASGFSFGDHAMHWVRQAPGKGL EWVSGISWNSGSIGYADSVKGRF TISRDNAKNSLYLQMNSLRAEDT AFYYCVPDSTSSKWGQGTLVTVS S | SEQ ID NO: 2<br>QSVLTQPASVSGSPGQSITISCTGTS SDVGKYTFVSWYQQHPGKAPKV MVYEVNKRPLGVSPRFSGSKSGNT AYLTISGLQAEDEADYYCSSYTSSS TVVFGGGTKLTVL |
| 2B12 | SEQ ID NO: 5<br>QVQLVQSGTEVKKPGASVRVSCK ASGYTFTSYYIHWVRQAPGQRLE WMGWINPNTGDTKYSHKFQGRV TMTRDTSINTTAYMDLSRLTSDDT AIYYCAPDSTSFGWGPGTLVTVSS | SEQ ID NO: 2<br>QSVLTQPASVSGSPGQSITISCTGTS SDVGKYTFVSWYQQHPGKAPKV MVYEVNKRPLGVSPRFSGSKSGNT AYLTISGLQAEDEADYYCSSYTSSS TVVFGGGTKLTVL |
| 2(E)6 | SEQ ID NO: 6<br>QMQLVQSGAEMKKSGESLKISCK ASGYTFGDTYIAWVRQTPGKGLE WMGSVYSSGSYTAYSPHFEGQVI LSVDKSTDTAYLQWSSLKASDTA IYYCARLEIASDGWIDSWGQGTL VTVSS | SEQ ID NO: 2<br>QSVLTQPASVSGSPGQSITISCTGTS SDVGKYTFVSWYQQHPGKAPKV MVYEVNKRPLGVSPRFSGSKSGNT AYLTISGLQAEDEADYYCSSYTSSS TVVFGGGTKLTVL |
| 2H5 | SEQ ID NO: 7<br>QITLKESGAEVKKPGSSVKVSCN ASGGIFRSQEISWVRQAPGQGLE WMGGIIPFIGTPNYAQKFQGRLTI TADESTNTAYMELRSLRSDDTAV YYCARGGRDGYNYQWMDYWG QGTLVTVSS | SEQ ID NO: 2<br>QSVLTQPASVSGSPGQSITISCTGTS SDVGKYTFVSWYQQHPGKAPKV MVYEVNKRPLGVSPRFSGSKSGNT AYLTISGLQAEDEADYYCSSYTSSS TVVFGGGTKLTVL |
| X18 | SEQ ID NO: 8<br>EVQLVQSGAEVKKPGASVRVSCK TSGYSGTSYDINWVRQTTGQLE WMGWVNPTSGSTGYAQKFQGR VTMTANTAINTAYMELRDLRSED TAVYFCVRDVPVDPWGQGTLVT VSS | SEQ ID NO: 9<br>QSVLTQPASVSGSPGQSITISCTGTS SDVGKYTFVSWYQQHPGKAPKV MVYEVNKRPLGVSPRFSGSKSGNT AYLTISGLQAEDEADYYCSSYASS STVVFGGGTKLTVL |
| X12 | SEQ ID NO: 10<br>QVQLVQSGAEVKKPGASVRVSC KTSGYSFTVYDINWVRQTTGQL EWMGWVNPTSGSTGYAQKFQGR VTMTANTAINTAYMELRDLRSED TAVYFCVRDVPVDPWGQGTTVT VSS | SEQ ID NO: 11<br>QSVLTQPASVSGSPGQSITISCTGTS SDVGKYLFVSWYQQHPGKAPKV MVYEVNKRPLGVSPRFSGSKSGNT AYLTISGLQAEDEADYYCSSYTSSS TVVFGGGTKLTVL |
| 2H5V | SEQ ID NO: 12<br>QITLKESGAEVKKPGASVKVSCK PSGYTFAGYNIHWVRQAPGQGLE WMGRINPNSGGTNYAQKFQGRV TMTRDTSISTAYMELSRLRSDDT AVYYCVRDNAKDSAPWGQGTLV TVSS | SEQ ID NO: 9<br>QSVLTQPASVSGSPGQSITISCTGTS SDVGKYTFVSWYQQHPGKAPKV MVYEVNKRPLGVSPRFSGSKSGNT AYLTISGLQAEDEADYYCSSYASS STVVFGGGTKLTVL |

We claim:

1. A fully human antibody that binds to *Staphylococcus aureus* autoinducing peptide-2 (AIP2), wherein the antibody comprises the heavy chain and light chain variable domain amino acid sequences of SEQ ID NO:4 and SEQ ID NO:2, respectively.

2. The fully human anti-AIP2 antibody of claim 1, comprising an IgG class antibody.

3. The fully human anti-AIP2 antibody of claim 1, comprising a Fab fully human anti-AIP2 antibody.

4. The fully human anti-AIP2 antibody of claim 1, comprising a single chain fully human anti-AIP2 antibody.

5. The fully human anti-AIP2 antibody of claim 1, wherein the antibody binds to autoinducing peptide-2 (AIP2) from a strain of group I of *Staphylococcus aureus*.

6. A pharmaceutical composition comprising the fully human antibody of claim 1 and a pharmaceutically acceptable carrier.

7. A method for binding an anti-AIP2 antibody to an AIP2 antigen, comprising: binding the anti-AIP2 antibody of claim 1 to a *Staphylococcus aureus* autoinducing peptide-2 (AIP2) protein to form a complex containing the anti-AIP2 antibody bound to the AIP2 protein, wherein the anti-AIP2 antibody is selected from a group consisting of a fully human antibody of an IgG class, a Fab fully human antibody or a single chain fully human antibody.

8. A method for pre-treating a subject prior to the subject having a *Staphylococcus aureus* infection, the method comprising: administering to the subject an effective amount of the anti-AIP2 antibody of claim 1, wherein the anti-AIP2 antibody is selected from a group consisting of a fully human antibody of an IgG class, a Fab fully human antibody or a single chain fully human antibody.

9. The method of claim 8, further comprising: monitoring the subject for any symptoms of infection associated with a *Staphylococcus aureus* autoinducing peptide-2 (AIP2).

10. The method of claim 8, wherein the infection associated with a *Staphylococcus aureus* autoinducing peptide-2 (AIP2) comprises methicillin-resistant *Staphylococcus aureus* (MRSA).

11. A method for treating a subject having a *Staphylococcus aureus* infection, the method comprising administering to the subject an effective amount of the anti-AIP2 antibody of claim 1, wherein the anti-AIP2 antibody is selected from a group consisting of a fully human antibody of an IgG class, a Fab fully human antibody or a single chain fully human antibody.

12. The method of claim 11, further comprising: monitoring the subject for any symptoms of infection associated with a *Staphylococcus aureus* autoinducing peptide-2 (AIP2).

13. The method of claim 11, wherein the infection associated with a *Staphylococcus aureus* autoinducing peptide-2 (AIP2) comprises methicillin-resistant *Staphylococcus aureus* (MRSA).

* * * * *

SEQUENCE LISTING

<160> NUMBER OF SEQ ID NOS: 12

<210> SEQ ID NO 1
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Gln Ser Gly Ala Glu Val Lys Lys Pro Gly Ala
1               5                   10                  15

Ser Val Arg Val Ser Cys Lys Thr Ser Gly Tyr Ser Phe Thr Ser Tyr
            20                  25                  30

Asp Ile Asn Trp Val Arg Gln Thr Thr Gly Gln Gly Leu Glu Trp Met
        35                  40                  45

Gly Trp Val Asn Pro Thr Ser Gly Ser Thr Gly Tyr Ala Gln Lys Phe
    50                  55                  60

Gln Gly Arg Val Thr Met Thr Ala Asn Thr Ala Ile Asn Thr Ala Tyr
65                  70                  75                  80

Met Glu Leu Arg Asp Leu Arg Ser Glu Asp Thr Ala Val Tyr Phe Cys
                85                  90                  95

Val Arg Asp Val Pro Phe Asp Pro Trp Gly Gln Gly Thr Leu Val Thr
            100                 105                 110

Val Ser Ser
        115

<210> SEQ ID NO 2
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Lys Tyr
            20                  25                  30

Thr Phe Val Ser Trp Tyr Gln Gln His Pro Gly Lys Ala Pro Lys Val
        35                  40                  45

Met Val Tyr Glu Val Asn Lys Arg Pro Leu Gly Val Ser Pro Arg Phe
    50                  55                  60

Ser Gly Ser Lys Ser Gly Asn Thr Ala Tyr Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Val Val Phe Gly Gly Gly Thr Lys Leu Thr Val Leu
            100                 105                 110

<210> SEQ ID NO 3
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Gln Val Gln Leu Val Gln Ser Gly Glu Leu Lys Lys Pro Gly Ala
1               5                   10                  15

Ser Val Lys Val Ser Cys Lys Ala Ser Gly Tyr Ser Phe Thr Thr Tyr
            20                  25                  30

Gly Ile His Trp Val Arg Gln Ala Pro Gly Gln Gly Leu Glu Trp Met
            35                  40                  45

Gly Trp Leu Asn Thr His Thr Glu His Pro Thr Tyr Ala Gln Gly Phe
        50                  55                  60

Thr Gly Arg Phe Val Leu Ser Leu Asp Thr Ser Val Ser Thr Ala Tyr
65                  70                  75                  80

Leu Gln Ile Thr Ser Leu Lys Ala Glu Asp Thr Ala Val Tyr Tyr Cys
                85                  90                  95

Val Arg Asp Asp Ser Phe Asp Pro Trp Gly Pro Gly Thr Leu Val Thr
            100                 105                 110

Val Ser Ser
        115

<210> SEQ ID NO 4
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Gly Asp His
            20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Phe Tyr Tyr Cys
                85                  90                  95

Val Pro Asp Ser Thr Ser Ser Lys Trp Gly Gln Gly Thr Leu Val Thr
            100                 105                 110

Val Ser Ser
        115

<210> SEQ ID NO 5
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Val Gln Ser Gly Thr Glu Val Lys Lys Pro Gly Ala
1               5                   10                  15

Ser Val Arg Val Ser Cys Lys Ala Ser Gly Tyr Thr Phe Thr Ser Tyr
            20                  25                  30

Tyr Ile His Trp Val Arg Gln Ala Pro Gly Gln Arg Leu Glu Trp Met
            35                  40                  45
```

Gly Trp Ile Asn Pro Asn Thr Gly Asp Thr Lys Tyr Ser His Lys Phe
            50                  55                  60

Gln Gly Arg Val Thr Met Thr Arg Asp Thr Ser Ile Asn Thr Ala Tyr
 65                  70                  75                  80

Met Asp Leu Ser Arg Leu Thr Ser Asp Asp Thr Ala Ile Tyr Tyr Cys
                85                  90                  95

Ala Pro Asp Ser Thr Ser Phe Gly Trp Gly Pro Gly Thr Leu Val Thr
            100                 105                 110

Val Ser Ser
        115

<210> SEQ ID NO 6
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Met Gln Leu Val Gln Ser Gly Ala Glu Met Lys Lys Ser Gly Glu
 1               5                  10                  15

Ser Leu Lys Ile Ser Cys Lys Ala Ser Gly Tyr Thr Phe Gly Asp Thr
                20                  25                  30

Tyr Ile Ala Trp Val Arg Gln Thr Pro Gly Lys Gly Leu Glu Trp Met
            35                  40                  45

Gly Ser Val Tyr Ser Ser Gly Ser Tyr Thr Ala Tyr Ser Pro His Phe
        50                  55                  60

Glu Gly Gln Val Ile Leu Ser Val Asp Lys Ser Thr Asp Thr Ala Tyr
 65                  70                  75                  80

Leu Gln Trp Ser Ser Leu Lys Ala Ser Asp Thr Ala Ile Tyr Tyr Cys
                85                  90                  95

Ala Arg Leu Glu Ile Ala Ser Asp Gly Trp Ile Asp Ser Trp Gly Gln
            100                 105                 110

Gly Thr Leu Val Thr Val Ser Ser
        115                 120

<210> SEQ ID NO 7
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Ile Thr Leu Lys Glu Ser Gly Ala Glu Val Lys Lys Pro Gly Ser
 1               5                  10                  15

Ser Val Lys Val Ser Cys Asn Ala Ser Gly Gly Ile Phe Arg Ser Gln
                20                  25                  30

Glu Ile Ser Trp Val Arg Gln Ala Pro Gly Gln Gly Leu Glu Trp Met
            35                  40                  45

Gly Gly Ile Ile Pro Phe Ile Gly Thr Pro Asn Tyr Ala Gln Lys Phe
        50                  55                  60

Gln Gly Arg Leu Thr Ile Thr Ala Asp Glu Ser Thr Asn Thr Ala Tyr
 65                  70                  75                  80

Met Glu Leu Arg Ser Leu Arg Ser Asp Asp Thr Ala Val Tyr Tyr Cys
                85                  90                  95

Ala Arg Gly Gly Arg Asp Gly Tyr Asn Tyr Gln Trp Met Asp Tyr Trp
            100                 105                 110

Gly Gln Gly Thr Leu Val Thr Val Ser Ser
        115                 120

<210> SEQ ID NO 8
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Val Gln Ser Gly Ala Glu Val Lys Lys Pro Gly Ala
1               5                   10                  15

Ser Val Arg Val Ser Cys Lys Thr Ser Gly Tyr Ser Gly Thr Ser Tyr
            20                  25                  30

Asp Ile Asn Trp Val Arg Gln Thr Thr Gly Gln Gly Leu Glu Trp Met
        35                  40                  45

Gly Trp Val Asn Pro Thr Ser Gly Ser Thr Gly Tyr Ala Gln Lys Phe
    50                  55                  60

Gln Gly Arg Val Thr Met Thr Ala Asn Thr Ala Ile Asn Thr Ala Tyr
65                  70                  75                  80

Met Glu Leu Arg Asp Leu Arg Ser Glu Asp Thr Ala Val Tyr Phe Cys
                85                  90                  95

Val Arg Asp Val Pro Val Asp Pro Trp Gly Gln Gly Thr Leu Val Thr
            100                 105                 110

Val Ser Ser
        115

<210> SEQ ID NO 9
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Lys Tyr
            20                  25                  30

Thr Phe Val Ser Trp Tyr Gln Gln His Pro Gly Lys Ala Pro Lys Val
        35                  40                  45

Met Val Tyr Glu Val Asn Lys Arg Pro Leu Gly Val Ser Pro Arg Phe
    50                  55                  60

Ser Gly Ser Lys Ser Gly Asn Thr Ala Tyr Leu Thr Ile Ser Gly Leu
65                  70                  75                  80

Gln Ala Glu Asp Glu Ala Asp Tyr Tyr Cys Ser Ser Tyr Ala Ser Ser
                85                  90                  95

Ser Thr Val Val Phe Gly Gly Gly Thr Lys Leu Thr Val Leu
            100                 105                 110

<210> SEQ ID NO 10
<211> LENGTH: 115
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 10

Gln Val Gln Leu Val Gln Ser Gly Ala Glu Val Lys Lys Pro Gly Ala
1               5                   10                  15

Ser Val Arg Val Ser Cys Lys Thr Ser Gly Tyr Ser Phe Thr Val Tyr
            20                  25                  30

Asp Ile Asn Trp Val Arg Gln Thr Thr Gly Gln Gly Leu Glu Trp Met
        35                  40                  45

Gly Trp Val Asn Pro Thr Ser Gly Ser Thr Gly Tyr Ala Gln Lys Phe
50                  55                  60

Gln Gly Arg Val Thr Met Thr Ala Asn Thr Ala Ile Asn Thr Ala Tyr
65                  70                  75                  80

Met Glu Leu Arg Asp Leu Arg Ser Glu Asp Thr Ala Val Tyr Phe Cys
                85                  90                  95

Val Arg Asp Val Pro Val Asp Pro Trp Gly Gln Gly Thr Thr Val Thr
            100                 105                 110

Val Ser Ser
        115

<210> SEQ ID NO 11
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Lys Tyr
            20                  25                  30

Leu Phe Val Ser Trp Tyr Gln Gln His Pro Gly Lys Ala Pro Lys Val
        35                  40                  45

Met Val Tyr Glu Val Asn Lys Arg Pro Leu Gly Val Ser Pro Arg Phe
50                  55                  60

Ser Gly Ser Lys Ser Gly Asn Thr Ala Tyr Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Val Val Phe Gly Gly Gly Thr Lys Leu Thr Val Leu
            100                 105                 110

<210> SEQ ID NO 12
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Ile Thr Leu Lys Glu Ser Gly Ala Glu Val Lys Lys Pro Gly Ala
1               5                   10                  15

Ser Val Lys Val Ser Cys Lys Pro Ser Gly Tyr Thr Phe Ala Gly Tyr
            20                  25                  30
```

-continued

```
Asn Ile His Trp Val Arg Gln Ala Pro Gly Gln Gly Leu Glu Trp Met
        35                  40                  45
Gly Arg Ile Asn Pro Asn Ser Gly Gly Thr Asn Tyr Ala Gln Lys Phe
    50                  55                  60
Gln Gly Arg Val Thr Met Thr Arg Asp Thr Ser Ile Ser Thr Ala Tyr
65                      70                  75                  80
Met Glu Leu Ser Arg Leu Arg Ser Asp Thr Ala Val Tyr Tyr Cys
                85                  90                  95
Val Arg Asp Asn Ala Lys Asp Ser Ala Pro Trp Gly Gln Gly Thr Leu
            100                 105                 110
Val Thr Val Ser Ser
        115
```